US008993841B2

(12) United States Patent
Napier et al.

(10) Patent No.: US 8,993,841 B2
(45) Date of Patent: Mar. 31, 2015

(54) FATTY ACID ELONGATION COMPONENTS AND USES THEREOF

(75) Inventors: Johnathan A. Napier, Preston (GB); Olga Sayanova, St. Albans (GB); Frederic Beaudoin, St. Albans (GB)

(73) Assignee: BASF Plant Science Company GmbH, Ludwigshafen (DE)

( * ) Notice: Subject to any disclaimer, the term of this patent is extended or adjusted under 35 U.S.C. 154(b) by 494 days.

(21) Appl. No.: 13/376,745

(22) PCT Filed: May 20, 2010

(86) PCT No.: PCT/EP2010/056936
§ 371 (c)(1), (2), (4) Date: Dec. 19, 2011

(87) PCT Pub. No.: WO2010/142522
PCT Pub. Date: Dec. 16, 2010

(65) Prior Publication Data

US 2012/0084889 A1 Apr. 5, 2012

(30) Foreign Application Priority Data

Jun. 8, 2009 (EP) .................................... 09162204

(51) Int. Cl.

| | |
|---|---|
| ***A01H 5/00*** | (2006.01) |
| ***C12N 15/82*** | (2006.01) |
| ***C12N 1/20*** | (2006.01) |
| ***C12N 15/00*** | (2006.01) |
| ***C12N 5/04*** | (2006.01) |
| ***C12P 7/64*** | (2006.01) |
| ***C12P 21/06*** | (2006.01) |
| ***C07H 21/04*** | (2006.01) |
| ***C12N 9/02*** | (2006.01) |
| ***C12N 9/88*** | (2006.01) |

(52) U.S. Cl.
CPC ............ *C12N 15/8247* (2013.01); *C12N 9/001* (2013.01); *C12N 9/88* (2013.01); *C12P 7/6427* (2013.01); *C12P 7/6472* (2013.01)
USPC ........ 800/281; 800/298; 435/320.1; 435/419; 435/252.3; 435/69.1; 435/134; 536/23.2

(58) Field of Classification Search
None
See application file for complete search history.

(56) References Cited

FOREIGN PATENT DOCUMENTS

| | | | |
|---|---|---|---|
| EP | 1790731 | A2 | 5/2007 |
| WO | WO-00/34439 | A1 | 6/2000 |
| WO | WO-00/75341 | A1 | 12/2000 |
| WO | WO-01/02591 | A1 | 1/2001 |
| WO | WO-01/59128 | A2 | 8/2001 |
| WO | WO-01/85968 | A2 | 11/2001 |
| WO | WO-02/26946 | A2 | 4/2002 |
| WO | WO-02/057465 | A2 | 7/2002 |
| WO | WO-02/077213 | A2 | 10/2002 |
| WO | WO-03/064638 | A2 | 8/2003 |
| WO | WO-03/072784 | A1 | 9/2003 |
| WO | WO-03/093482 | A2 | 11/2003 |
| WO | WO-2004/057001 | A2 | 7/2004 |
| WO | WO-2004/090123 | A2 | 10/2004 |
| WO | WO-2005/012316 | A2 | 2/2005 |
| WO | WO-2005/083053 | A2 | 9/2005 |
| WO | WO-2005/083093 | A2 | 9/2005 |
| WO | WO-2006/069710 | A1 | 7/2006 |
| WO | WO-2006/100241 | A2 | 9/2006 |
| WO | WO-2007/042510 | A2 | 4/2007 |
| WO | WO-2007/093776 | A2 | 8/2007 |
| WO | WO-2007/106903 | A2 | 9/2007 |
| WO | WO-2008/006202 | A1 | 1/2008 |
| WO | WO-2008/022963 | A2 | 2/2008 |
| WO | WO-2008/040787 | A2 | 4/2008 |
| WO | WO-2009/016202 | A2 | 2/2009 |
| WO | WO-2009/016208 | A2 | 2/2009 |
| WO | WO-2009/133145 | A1 | 11/2009 |

OTHER PUBLICATIONS

Doerks et al, TIG 14(6): 248-250, Jun. 1998.*
Brenner, S.E., TIG 15(4):132-133, Apr. 1999.*
Bork et al, TIG 12(10): 425-427, Oct. 1996.*
Armbrust, E.V., et al., "The Genome of the Diatom *Thalassiosire Pseudonana*: Ecology, Evolution, and Metabolism", Science, 2004, vol. 306, pp. 79-86.
Arondel, V., et a., "The Map-Based Cloning of a Gene Controlling Omega-3 Fatty Acid Desaturation in *Arabidopsis*", Science, 1992, vol. 258, pp. 1353-1355.
Bowler, C., et al. "The *Phaeodactylum* Genome Reveals the Evolutionary History of Diatom Genomes", Nature, 2008, vol. 456, pp. 239-244.
Broadwater, J.A., et al., "Desaturation and Hydroxylation", The Journal of Biological Chemisty, 2002, vol. 277, No. 18, pp. 15613-15620.
Broun, P., et al., "Catalytic Plasticity of Fatty Acid Modification Enzymes Underlying Chemical Diversity of Plant Lipids", Science, 1998, vol. 282, pp. 1315-1317.
Calvo, A.M., et al., "Genetic Connection Between Fatty Acid *Aspergillus nidulans*", The Journal of Biological Chemistry, 2001, vol. 276, No. 28, Issue of Jul. 13, pp. 25766-25774.
Crawford, M.A., et al., "Are Deficits of Arachidonic and Docosahexaenoic Responsible for the Neural and Vascular Complications of Preterm Babies", Am. J. Clin. Nutr., 1997. vol. 66 pp. 1032S-1041S.
Deblaere, R., et al., "Efficient Octopine Ti Plasmid-Derived Vectors for *Agrobacterium*-mediated Gene Transfer to Plants". Nucleic Acids Research, 1935, vol, 13, No. 13, pp. 4777-4788.

(Continued)

*Primary Examiner* — Elizabeth McElwain
(74) *Attorney, Agent, or Firm* — Drinker Biddle & Reath LLP

(57) ABSTRACT

The invention provides isolated nucleic acid molecules which encodes a novel fatty acid nECR. The invention also provides recombinant expression vectors containing nECR nucleic acid molecules, host cells into which the expression vectors have been introduced, and methods for large-scale production of long chain polyunsaturated fatty acids (LCPUFAs), e.g., ARA, EPA and DHA.

17 Claims, 12 Drawing Sheets

(56) References Cited

OTHER PUBLICATIONS

Giusto, N.M., et al,, "Lipid Metabolism in Vertebrate Retinal Rod Outer Segments", Progress in Lipid Research, 2000, vol. 39, pp. 315-391.
Horrocks, L.A., et al., Health Benefits of Docosahexaenoic Acid (DHA), Pharmacological Research, 1999, vol. 40, No. 3, pp. 211-215.
Knutzon, D.S., et al., "Identification of Δ5-Desaturase from *Mortierella alpina* by Heterologous Expression in Bakers' Yeast and Canola", The Journal of Biological Chemistry, 1998, vol. 273, No. 45. Issue of Nov. 6, pp. 29360-29366.
Mantle, P.G., et al., "Differentiation of *Clavieps purpurea* in Axenic Culture", Journal of General Microbiology, 1976, vol. 93, pp. 321-334.
Martinez, M. et al., "Tissue Levels to Polyunsaturated Fatty Acids During Early Human Development", J. Pediatr., 1992. vol. 120, pp. S129-S138.
Mey, G., et al., "The Biotrophic Non-Appressorium-Forming Grass Pathogen *Claviceps purpurea* Needs a *Fus3/Pmk1* Homologous Mitogen-Activated Protein Kinase for Colonization of Rye Ovarian Tissue", MPMI, 2002, vol. 15, No. 4, pp. 303-312.
Napier, J.A., "The Production of Unusual Fatty Acids in Transgenic Plants", Annu. Rev. Plant Biol., 2007, vol. 58, pp. 295-319.
Ohlrogge, J., et al., "Lipid Biosynthesis", The Plant Cell, 1995, vol. 7, pp. 957-970.
Okuley, J., et al., "Arabidopsis *FAD2* Gene Encodes the Enzyme That is Essential for Polyunsaturated Lipid Synthesis", The Plant Cell, 1994, vol. 6, pp. 147-158.
Qi, B., et al., "Production of Very Long Chain Polyunsaturated Omega-3 and Omega-6 Fatty Acids in Plants", Nature Biotechnology, 2004, vol. 22, No. 6, pp. 739-745.
Qiu, X., et al., "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*", The Journal of Biological Chemistry, 2001, vol. 276, No. 34, Issue of Aug. 24, pp. 31561-31566.
Shanklin, J., et al., "Desaturation and Related Modifications of fatty Acids", Annu. Rev. Plant Physiol. Plant Mol. Biol., 1998, vol. 46, pp. 611-641.
Spector, A.A., "Essentially of Fatty Acids", Lipids, 1999, vol. 34, pp. S1-S3.
Tonon, T., et al., "Fatty Acid Desaturases from the Microalga *Thalassiosira pseudonana*", FEBS Journal, 2005, vol. 272, pp. 3401-3412.
Tudzynski, P., et al., "Biotechnology and Genetics of Ergot Alkaloids", Appl. Microbiol. Biotechnol., 2001, vol. 57, pp. 593-605.
"B7FVT1_PHATC", EMBL Database, Accession No. B7FVT1, Feb. 10, 2009.
"B5YMG6_THAPS", Uniprot Database, Accession No. B5YMG6, Nov. 25, 2008.

* cited by examiner

Fig. 1

```
   1 M   A   A   A   K   Q   Q   Q   S   K   G   L   G   L   K   D   L   Y   L   I
   1 atggctgctgctaaacaacaacagtctaagggacttggacttaaggatctctaccttata
   1 taccgacgacgatttgttgttgtcagattccctgaacctgaattcctagagatggaatat
  21 T   Y   N   A   L   C   C   L   G   W   A   Y   V   L   A   L   G   I   P   T
  61 acttacaacgctttgtgttgtcttggatgggcttacgttcttgctcttggaatccctacc
  61 tgaatgttgcgaaacacaacagaacctacccgaatgcaagaacgagaaccttagggatgg
  41 F   I   A   S   V   T   S   S   I   G   T   S   S   L   V   E   S   L   K   I
 121 tttatcgcttctgtgacctcttctatcggaacttctagccttgttgagtctcttaagatc
 121 aaatagcgaagacactggagaagatagccttgaagatcggaacaactcagagaattctag
  61 A   G   R   S   V   Y   A   A   T   P   Y   T   A   G   W   S   N   E   A   T
 181 gctggaagatctgtttacgctgctactccttacactgctggatggtctaacgaggctact
 181 cgaccttctagacaaatgcgacgatgaggaatgtgacgacctaccagattgctccgatga
  81 P   S   L   A   T   V   L   M   Y   V   Q   S   A   A   V   L   E   I   V   H
 241 ccttctcttgctaccgttcttatgtacgttcagtctgctgctgttcttgagatcgttcac
 241 ggaagagaacgatggcaagaatacatgcaagtcagacgacgacaagaactctagcaagtg
 101 A   A   L   G   L   V   R   S   P   V   F   V   T   T   M   Q   V   G   S   R
 301 gctgctcttggacttgttagatctcctgttttcgtgaccactatgcaagttggatcaaga
 301 cgacgagaacctgaacaatctagaggacaaaagcactggtgatacgttcaacctagttct
 121 I   V   A   L   H   M   L   S   T   C   P   S   A   Q   T   Q   W   G   A   A
 361 atcgttgctctccatatgctttctacttgtccttctgctcaaactcaatggggagctgct
 361 tagcaacgagaggtatacgaaagatgaacaggaagacgagtttgagttacccctcgacga
 141 L   M   I   F   S   W   A   L   V   E   V   P   R   Y   L   F   Y   V   A   A
 421 cttatgatcttctcttgggctcttgttgaagttcctcgttacctcttctacgttgctgct
 421 gaatactagaagagaacccgagaacaacttcaaggagcaatggagaagatgcaacgacga
 161 I   V   T   G   D   A   T   K   G   T   P   Y   P   L   F   W   L   R   Y   S
 481 atcgttactggtgatgctactaagggaactccttaccctttgttctggctcagatactct
 481 tagcaatgaccactacgatgattcccttgaggaatgggaaacaagaccgagtctatgaga
 181 L   F   A   V   L   Y   P   T   G   I   S   G   E   L   S   V   F   L   T   S
 541 cttttcgctgttctttaccctactggaatctctggtgagttgtctgttttcctcacttct
 541 gaaaagcgacaagaaatgggatgaccttagagaccactcaacagacaaaaggagtgaaga
 201 A   K   C   D   T   F   L   S   T   L   G   E   S   N   K   S   I   M   Y   W
 601 gctaagtgcgataccttcctttctaccctcggtgaaagcaacaagtctattatgtactgg
 601 cgattcacgctatggaaggaaagatgggagccactttcgttgttcagataatacatgacc
 221 Y   A   M   A   F   P   I   I   Y   A   P   G   A   L   P   M   I   F   N   M
 661 tacgctatggctttccctattatctacgctcctggtgctctccctatgatcttcaatatg
 661 atgcgataccgaaagggataatagatgcgaggaccacgagagggatactagaagttatac
 241 V   A   N   R   K   S   A   M   K   K   R   F   A   R   P   P   P   P   P   R
 721 gtggctaaccgtaagtctgctatgaagaagagattcgctagacctcctccacctcctaga
 721 caccgattggcattcagacgatacttcttctctaagcgatctggaggaggtggaggatct
 261 G   L   V   W   P   V   T   E   T   K   A   N   G   E   E   V   R   S   S   T
 781 ggacttgtttggcctgttactgagactaaggctaacggtgaagaagttagatcttctacc
 781 cctgaacaaaccggacaatgactctgattccgattgccacttcttcaatctagaagatgg
 281 P   V   A   K   E   I   L   A   A   A   I   G   A   V   N   P   E   L   A   E
 841 cctgtggctaaagagatccttgctgctgctatcggagctgttaaccctgagcttgctgag
 841 ggacaccgatttctctaggaacgacgacgatagcctcgacaattgggactcgaacgactc
 301 K   V   R   N   E   K   K   W   R   F   G   Y   Q   K   H   L   V   N   M   V
 901 aaagtgagaaacgagaagaagtggagattcggataccaaaagcacctcgtgaatatggtt
 901 tttcactctttgctcttcttcacctctaagcctatggttttcgtggagcacttataccaa
 321 E   A   Q   C   K   S   P   E   D   A   L   K   I   A   N   A   G   L   N   K
 961 gaggctcagtgtaagtctcctgaggatgctcttaagattgctaacgccggacttaacaag
 961 ctccgagtcacattcagaggactcctacgagaattctaacgattgcggcctgaattgttc
 341 A   Y   M   T   F   Q   F   V   S   S   D   G   S   K   T   T   T   F   A   E
1021 gcttatatgaccttccagttcgtttcttctgatggatctaagactactactttcgctgag
1021 cgaatatactggaaggtcaagcaaagaagactacctagattctgatgatgaaagcgactc
```

Fig. 1 (Continued)

```
 361 A  M  S  S  K  S  S  D  K  F  H  T  G  F  I  K  G  E  L  A
1081 gctatgtctagcaagtctagcgataagttccacactggttttatcaagggtgaactcgct
1081 cgatacagatcgttcagatcgctattcaaggtgtgaccaaaatagttcccacttgagcga
 381 P  Q  K  E  K  K  L  E  V  G  Y  K  G  K  Q  I  S  G  D  E
1141 cctcaaaaagagaagaagctcgaagttggatacaagggaaagcagatctctggtgatgag
1141 ggagtttttctcttcttcgagcttcaacctatgttccctttcgtctagagaccactactc
 401 L  K  A  Q  V  K  E  W  V  D  Y  G  T  I  E  P  S  A  G  E
1201 cttaaggctcaagtgaaagagtgggttgactacggaactatcgagccttctgctggtgaa
1201 gaattccgagttcactttctcacccaactgatgccttgatagctcggaagacgaccactt
 421 A  I  C  S  C  V  D  N  P  G  W  I  D  L  S  D  R  Y  F  V
1261 gctatctgttcttgcgttgataaccctggatggatcgatctttctgacagatacttcgtt
1261 cgatagacaagaacgcaactattgggacctacctagctagaaagactgtctatgaagcaa
 441 L  L  G  A  G  S  A  M  G  P  F  E  V  L  M  Q  L  G  A  N
1321 cttcttggagctggatctgctatgggacctttcgaggttttgatgcaacttggagctaac
1321 gaagaacctcgacctagacgataccctggaaagctccaaaactacgttgaacctcgattg
 461 V  I  G  I  D  L  D  R  P  F  I  W  Q  R  L  I  N  R  V  M
1381 gttatcggaatcgacctcgacagacctttttatctggcagaggcttatcaacagagtgatg
1381 caatagccttagctggagctgtctggaaaatagaccgtctccgaatagttgtctcactac
 481 N  S  S  G  S  I  T  F  P  M  S  K  E  Q  S  K  C  A  D  E
1441 aactcttctggatctatcaccttccctatgtctaaagaacagagcaagtgcgctgatgag
1441 ttgagaagacctagatagtggaagggatacagatttcttgtctcgttcacgcgactactc
 501 K  E  L  F  A  A  S  G  C  N  L  F  T  Q  A  P  M  I  R  D
1501 aaagagcttttcgctgcttctggatgcaacctttttcactcaggctcctatgatcagagat
1501 tttctcgaaaagcgacgaagacctacgttggaaaagtgagtccgaggatactagtctcta
 521 W  L  V  D  L  Y  P  G  K  S  F  T  V  G  S  Y  A  Y  L  N
1561 tggctcgttgatctttaccctggaaagtctttcactgtgggatcttacgcttaccttaac
1561 accgagcaactagaaatgggacctttcagaaagtgacaccctagaatgcgaatggaattg
 541 G  A  L  H  V  Q  V  S  L  A  M  D  A  I  C  R  D  L  C  D
1621 ggtgctctccacgttcaagtttctcttgctatggatgctatctgtcgtgatctctgcgat
1621 ccacgagaggtgcaagttcaaagagaacgatacctacgatagacagcactagagacgcta
 561 K  R  K  N  T  S  L  A  Y  L  C  T  P  T  D  L  H  L  I  P
1681 aagaggaagaacacttctcttgcttacctctgcactcctactgatcttcaccttatccct
1681 ttctccttcttgtgaagagaacgaatggagacgtgaggatgactagaagtggaataggga
 581 K  E  A  H  D  A  A  E  A  N  Y  K  E  F  S  K  K  P  F  C
1741 aaagaggctcacgacgctgctgaggctaactacaaagagttcagcaagaaacctttctgt
1741 tttctccgagtgctgcgacgactccgattgatgtttctcaagtcgttctttggaaagaca
 601 M  F  M  K  L  F  F  G  K  K  T  L  R  K  N  V  K  K  P  V
1801 atgtttatgaagttgttcttcggaaagaaaaccctcagaaagaacgtgaagaagcctgtt
1801 tacaaatacttcaacaagaagcctttcttttgggagtctttcttgcacttcttcggacaa
 621 S  G  V  G  G  D  F  Y  Y  V  N  G  I  S  V  A  Q  G  P  N
1861 agcggagttggtggagatttctactacgtgaacggaatctctgttgctcaaggacctaac
1861 tcgcctcaaccacctctaaagatgatgcacttgccttagagacaacgagttcctggattg
 641 Y  A  L  A  K  R  M  Q  H  W  R  A  V  I  A  R  S  K  G  C
1921 tacgctcttgctaagagaatgcaacactggcgtgctgttatcgctagaagcaagggatgt
1921 atgcgagaacgattctcttacgttgtgaccgcacgacaatagcgatcttcgttccctaca
 661 I  V  S  S  N  I  A  P  S  T  S  T  V  S  V  T  Q  N  R  T
1981 atcgtgtctagcaatatcgctccttctacctctactgtttctgtgactcagaacagaact
1981 tagcacagatcgttatagcgaggaagatggagatgacaaagacactgagtcttgtcttga
 681 F  A  W  A  Y  E  G  M  P  Y  F  K  P  Y  E  I  F  A  P  E
2041 ttcgcttgggcttacgagggaatgccttacttcaagccttacgagatcttcgctcctgag
2041 aagcgaacccgaatgctcccttacggaatgaagttcggaatgctctagaagcgaggactc
 701 T  S  N  S  V  M  S  A  I  L  F  N  D  L  N  N  H  K  S  I
2101 acttctaactctgtgatgagcgctatccttttcaacgatctcaacaaccacaagtctatc
2101 tgaagattgagacactactcgcgataggaaaagttgctagagttgttggtgttcagatag
```

Fig. 1 (Continued)

```
 721 A  N  P  D  V  G  I  A  N  P  N  Q  L  F  S  F  G  A  F  H
2161 gctaaccctgatgttggaatcgctaacccaaaccagcttttctctttcggtgctttccac
2161 cgattgggactacaaccttagcgattgggtttggtcgaaaagagaaagccacgaaaggtg
 741 G  G  T  W  R  C  A  Y  E  I  D  S  I  G  E  A  S  V  L  L
2221 ggtggaacttggagatgtgcttacgagattgattctatcggagaggcttctgttcttctc
2221 ccaccttgaacctctacacgaatgctctaactaagatagcctctccgaagacaagaagag
 761 Y  F  S  R  V  A  K  P  Y  A  I  A  F  G  G  L  G  L  A  A
2281 tacttctctcgtgttgctaaaccttacgctatcgctttcggaggacttggtctagctgct
2281 atgaagagagcacaacgatttggaatgcgatagcgaaagcctcctgaaccagatcgacga
 781 G  A  K  W  F  G  I  V  *
2341 ggtgctaagtggttcggaattgtgtga
2341 ccacgattcaccaagccttaacacact
```

Fig. 2

```
   1 M   G   L   K   D   A   Y   L   V   L   Y   N   S   A   C   C   A   G   W   A
   1 atgggacttaaggacgcttacctcgtgctttacaactctgcttgttgtgctggctgggct
   1 taccctgaattcctgcgaatggagcacgaaatgttgagacgaacaacacgaccgacccga
  21 Y   V   W   Y   A   A   C   T   T   I   L   D   K   V   A   N   Q   S   P   F
  61 tatgtttggtacgctgcttgtactactatcctcgataaggttgcaaaccagtcacctttc
  61 atacaaaccatgcgacgaacatgatgataggagctattccaacgtttggtcagtggaaag
  41 G   D   A   S   A   Q   V   Y   A   H   D   D   T   A   T   M   L   T   Y   A
 121 ggtgatgcttctgctcaagtttacgctcacgatgatactgctactatgcttacctacgct
 121 ccactacgaagacgagttcaaatgcgagtgctactatgacgatgatacgaatggatgcga
  61 Q   S   A   A   L   L   E   I   L   H   A   A   L   G   L   V   R   S   P   V
 181 caatctgctgctctccttgagatccttcacgctgctcttggacttgttagatctcctgtt
 181 gttagacgacgagaggaactctaggaagtgcgacgagaacctgaacaatctagaggacaa
  81 M   V   T   A   M   Q   V   M   S   R   I   V   A   L   V   A   L   V   F   S
 241 atggtgaccgctatgcaagttatgtctaggatcgttgctcttgttgctctcgtgttctct
 241 taccactggcgatacgttcaatacagatcctagcaacgagaacaacgagagcacaagaga
 101 S   Q   A   Q   T   Q   W   G   A   G   L   M   I   I   S   W   A   S   V   E
 301 tcacaagctcaaactcaatggggagctggacttatgattatctcttgggcttcagttgaa
 301 agtgttcgagtttgagttacccctcgacctgaatactaatagagaacccgaagtcaactt
 121 V   P   R   Y   A   F   Y   V   T   A   L   L   T   G   D   A   T   K   K   T
 361 gttcctcgttacgctttctacgttactgctctccttactggtgatgctactaagaaaacc
 361 caaggagcaatgcgaaagatgcaatgacgagaggaatgaccactacgatgattcttttgg
 141 P   F   P   L   F   W   L   R   Y   S   L   F   A   I   L   Y   P   T   G   I
 421 cctttccctcttttctggcttcgttactctcttttcgctatcctttaccctactggaatc
 421 ggaaagggagaaaagaccgaagcaatgagagaaaagcgataggaaatgggatgaccttag
 161 C   G   E   L   T   V   F   L   A   A   S   K   D   Q   A   F   V   D   K   F
 481 tgtggagagcttactgttttcctcgctgcttctaaggatcaagctttcgtggataagttc
 481 acacctctcgaatgacaaaaggagcgacgaagattcctagttcgaaagcacctattcaag
 181 G   P   L   S   V   T   L   Y   S   I   V   L   P   I   V   Y   F   F   G   S
 541 ggacctctttctgttactctctactctatcgttctccctatcgtgtacttcttcggatct
 541 cctggagaaagacaatgagagatgagatagcaagagggatagcacatgaagaagcctaga
 201 P   F   M   I   M   N   M   V   A   N   R   K   S   A   F   K   K   R   F   A
 601 ccttttatgattatgaatatggtggctaacagaaagtctgctttcaagaagagattcgca
 601 ggaaaatactaatacttataccaccgattgtctttcagacgaaagttcttctctaagcgt
 221 K   P   P   P   P   A   R   G   L   C   W   P   V   D   A   K   G   Q   R   S
 661 aagcctccacctcctgctagaggactttgttggcctgttgatgctaagggacagagatct
 661 ttcggaggtggaggacgatctcctgaaacaaccggacaactacgattccctgtctctaga
 241 S   T   N   V   N   K   T   I   I   A   A   A   V   G   A   V   N   E   Q   K
 721 tctaccaacgtgaacaagacgattattgctgctgctgttggagctgttaacgagcaaaag
 721 agatggttgcacttgttctgctaataacgacgacgacaacctcgacaattgctcgttttc
 261 A   E   A   I   R   S   C   K   A   W   R   F   Q   Y   V   K   H   L   R   A
 781 gctgaggctatcagatcttgtaaggcttggagattccagtacgttaagcaccttagagct
 781 cgactccgatagtctagaacattccgaacctctaaggtcatgcaattcgtggaatctcga
 281 M   V   E   E   Q   C   Q   T   P   E   S   A   L   K   I   A   Q   A   G   L
 841 atggttgaggaacaatgtcaaactcctgagtctgctcttaagatcgctcaagctggactt
 841 taccaactccttgttacagtttgaggactcagacgagaattctagcgagttcgacctgaa
 301 D   S   A   Y   D   I   F   E   F   V   A   P   D   G   S   A   T   T   F   R
 901 gattctgcttacgatatcttcgagttcgttgctcctgatggatctgctactactttcagg
 901 ctaagacgaatgctatagaagctcaagcaacgaggactacctagacgatgatgaaagtcc
 321 E   A   M   A   A   K   N   T   E   Q   F   F   T   H   V   I   K   G   E   G
 961 gaagctatggctgctaagaacactgagcagttcttcactcacgttatcaagggagaggga
 961 cttcgataccgacgattcttgtgactcgtcaagaagtgagtgcaatagttccctctccct
 341 N   K   L   T   K   E   L   E   I   P   Y   K   G   G   I   L   K   G   D   A
1021 aacaagcttaccaaagagcttgagatcccttacaagggtggaatccttaagggtgatgct
1021 ttgttcgaatggtttctcgaactctagggaatgttcccaccttaggaattcccactacga
 361 L   K   K   Q   V   Q   S   W   A   D   Y   G   T   I   E   P   S   A   G   A
1081 cttaagaagcaggttcagtcttgggctgattacggaactatcgagccttctgctggtgct
1081 gaattcttcgtccaagtcagaacccgactaatgccttgatagctcggaagacgaccacga
```

Fig. 2 (Continued)

```
 381 A  I  V  K  C  I  E  H  P  E  W  L  D  I  S  N  R  Y  F  V
1141 gctatcgttaagtgtatcgagcaccctgagtggcttgatatcagcaacagatacttcgtt
1141 cgatagcaattcacatagctcgtgggactcaccgaactatagtcgttgtctatgaagcaa
 401 L  L  G  A  G  S  A  M  G  P  L  L  V  L  M  A  L  G  A  N
1201 cttcttggagctggatctgctatgggacctcttcttgttcttatggctctcggagctaac
1201 gaagaacctcgacctagacgataccctggagaagaacaagaataccgagagcctcgattg
 421 V  I  A  V  D  L  D  R  P  N  I  W  K  R  L  I  D  I  A  R
1261 gttatcgctgtggatcttgatagacctaatatctggaagcgtcttatcgatatcgctaga
1261 caatagcgacacctagaactatctggattatagaccttcgcagaatagctatagcgatct
 441 Q  S  S  G  T  I  T  F  P  M  K  M  D  P  S  K  C  K  N  D
1321 caatcttctggaacgatcaccttccctatgaagatggaccctagcaagtgtaagaacgac
1321 gttagaagaccttgctagtggaagggatacttctacctgggatcgttcacattcttgctg
 461 E  E  M  F  A  Q  A  G  C  N  L  F  T  D  T  P  M  I  R  D
1381 gaggaaatgttcgctcaggctggatgtaaccttttcaccgacacccctatgatcagagat
1381 ctcctttacaagcgagtccgacctacattggaaaagtggctgtggggatactagtctcta
 481 W  L  M  N  V  Y  P  G  K  S  L  T  V  G  C  Y  A  Y  L  D
1441 tggttgatgaacgtttaccctggaaagtctcttactgttggatgctacgcttaccttgat
1441 accaactacttgcaaatgggacctttcagagaatgacaacctacgatgcgaatggaacta
 501 G  A  L  H  V  Q  V  S  L  A  M  D  A  I  C  R  D  L  S  E
1501 ggtgctctccacgttcaagtttctcttgctatggatgctatctgccgtgatctttctgag
1501 ccacgagaggtgcaagttcaaagagaacgatacctacgatagacggcactagaaagactc
 521 K  R  K  N  T  S  L  A  Y  L  C  T  P  T  D  L  H  L  I  P
1561 aagaggaagaacacttctcttgcttacctctgcactcctactgatcttcacttgatccct
1561 ttctccttcttgtgaagagaacgaatggagacgtgaggatgactagaagtgaactaggga
 541 K  E  A  H  D  A  M  K  A  N  Y  K  S  Y  S  G  K  L  Y  C
1621 aaagaggctcacgatgctatgaaggctaactacaagtcttactccggaaagctttactgt
1621 tttctccgagtgctacgatacttccgattgatgttcagaatgaggcctttcgaaatgaca
 561 M  M  M  N  L  L  S  G  G  K  F  L  R  Q  N  S  K  K  P  V
1681 atgatgatgaaccttctcagcggaggaaagttccttagacagaactctaagaagcctgtt
1681 tactactacttggaagagtcgcctcctttcaaggaatctgtcttgagattcttcggacaa
 581 S  G  K  G  G  E  Y  Y  L  V  N  G  I  S  V  A  Q  G  P  N
1741 tctggaaagggtggagagtactaccttgtgaacggaatctctgttgctcaaggacctaac
1741 agacctttcccacctctcatgatggaacacttgccttagagacaacgagttcctggattg
 601 Y  A  L  A  K  R  M  Q  H  W  R  A  I  T  A  R  N  K  G  C
1801 tacgctcttgctaagagaatgcaacactggcgtgctatcactgctagaaacaagggatgt
1801 atgcgagaacgattctcttacgttgtgaccgcacgatagtgacgatctttgttccctaca
 621 I  V  S  S  N  I  A  P  S  T  S  T  V  S  V  V  H  N  R  T
1861 atcgtgtctagcaatattgctccttctacctctaccgtttctgttgttcacaacagaact
1861 tagcacagatcgttataacgaggaagatggagatggcaaagacaacaagtgttgtcttga
 641 F  A  W  A  Y  E  G  M  P  Y  F  E  P  F  E  I  F  A  P  E
1921 ttcgcttgggcttacgagggaatgccttacttcgagcctttcgagatcttcgctcctgag
1921 aagcgaacccgaatgctcccttacggaatgaagctcggaaagctctagaagcgaggactc
 661 T  S  N  A  V  M  S  A  L  L  F  Y  D  L  N  D  S  G  S  W
1981 acttctaacgctgttatgtctgctctcctcttctacgatctcaacgattctggatcttgg
1981 tgaagattgcgacaatacagacgagaggagaagatgctagagttgctaagacctagaacc
 681 A  T  P  N  T  S  L  G  N  P  N  Q  L  F  S  H  G  S  F  H
2041 gctactcctaacacttctctcggaaaccctaaccagcttttctctcacggatctttccac
2041 cgatgaggattgtgaagagagcctttgggattggtcgaaaagagagtgcctagaaaggtg
 701 G  G  V  W  R  C  A  Y  E  V  D  S  I  G  E  S  S  V  L  L
2101 ggtggagtttggagatgtgcttacgaggttgactctatcggagaatcttctgtgcttctc
2101 ccacctcaaacctctacacgaatgctccaactgagatagcctcttagaagacacgaagag
 721 Y  F  G  R  V  A  K  P  Y  M  V  A  A  G  A  V  A  A  A  G
2161 tacttcggaagagtggctaaaccttatatggttgctgctggtgccgtggccgcagctggt
2161 atgaagccttctcaccgatttggaatataccaacgacgaccacggcaccggcgtcgacca
 741 A  A  Y  V  Y  A  V  *
2221 gcagcctacgtttacgctgtgtga
2221 cgtcggatgcaaatgcgacacact
```

Fig. 4

| | YDL015C | nECR(Pt) | nECR(Tp) | YJL097w |
|---|---|---|---|---|
| YDL015C | | 8 | 8 | 12 |
| nECR(Pt) | | | 65 | 25 |
| nECR(Tp) | | | | 27 |
| YJL097w | | | | |

A
pYES-d9Elo(Ig)
<5% conversion
16:1
16:0
18:1
18:3
20:3
10
15
20
B
pYES-d9Elo(Ig) +
pESC-nECR(Tp)
42% conversion
10
15
20

FATTY ACID ELONGATION COMPONENTS AND USES THEREOF

RELATED APPLICATIONS

This application is a national stage application (under 35 U.S.C. §371) of PCT/EP2010/056936, filed May 20, 2010 which claims benefit of European Application No. 09162204.3 filed Jun. 8, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418 __00078 U.S. The size of the text file is 72 KB and the text file was created on Dec. 5, 2011.

The invention in principle pertains to the field of recombinant manufacture of fatty acids. It provides nucleic acid molecules which encode novel fatty acid dehydratase/enoyl-CoA reductase (nECR) family members. The invention also provides recombinant expression vectors containing nECR nucleic acid molecules, host cells into which the expression vectors have been introduced, and methods for large-scale production of long chain polyunsaturated fatty acids (LCPUFAs), e.g. ARA, EPA and DHA.

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et at., 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2), linolenic acid (C18:3). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al, (1997) Am. J. Clin. Nutr. 66:1032S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120: S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and ARA are both essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the ω-3 position confers on ARA different properties than those found in EPA. The eicosanoids produced from AA have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as DHA, EPA and ARA.

Thus, the present invention relates to a polynucleotide comprising a nucleic acid sequence elected from the group consisting of:

a) a nucleic acid sequence having a nucleotide sequence as shown in SEQ ID NOs: 1 or 3;

b) a nucleic acid sequence encoding a polypeptide having an amino acid sequence as shown in SEQ ID NOs: 2 or 4;

c) a nucleic acid sequence being at least 50% identical to the nucleic acid sequence of a) or b), wherein said nucleic acid sequence encodes a polypeptide having dehydratase/enoyl-CoA reductase (nECR) activity;

d) a nucleic acid sequence encoding a polypeptide having nECR activity and having an amino acid sequence which is at least 50% identical to the amino acid sequence of any one of a) to c); and e) a nucleic acid sequence which is capable of hybridizing under stringent conditions to any one of a) to d), wherein said nucleic acid sequence encodes a polypeptide having nECR activity.

The term "polynucleotide" as used in accordance with the present invention relates to a polynucleotide comprising a nucleic acid sequence which encodes a polypeptide having dehydratase/enoyl-CoA reductase (nECR) activity. Preferably, the polypeptide encoded by the polynucleotide of the present invention having nECR activity upon expression in a plant shall be capable of increasing the amount of PUFA and, in particular, LCPUFA in, e.g., seed oils or the entire plant or parts thereof. Such an increase is, preferably, statistically significant when compared to a LCPUFA producing transgenic control plant which expresses the minimal set of desaturases and elongases required for LCPUFA synthesis but does not express the polynucleotide of the present invention. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to said control. Preferably, the LCPUFA referred to before is a polyunsaturated fatty acid having a C-20, C-22 or C24 fatty acid body, more preferably, ARA, EPA or DHA. Suitable assays for measuring the activities mentioned before are described in the accompanying Examples.

The term "nECR activity" or "dehydratase/enoyl-CoA reductase activity" as used herein refers to the combined activity of a enoyl-CoA reductase and a dehydratase, i.e. the enzyme having the combined activity shall be capable of removing a hydroxyl group from 3-hydroxy-acyl-CoA and reducing the formed double bond as part of the elongation process for fatty acids. Fatty acid elongation is catalyzed in four steps, represented by four enzymes: KCS (keto-acyl-CoA-synthase), KCR (keto-acyl-CoA-reductase), DH (dehydratase) and ECR (enoyl-CoA-reductase). In the first step a fatty acid-CoA ester is condensed with malonyl-CoA producing a keto-acly-CoA intermediate, which is elongated by two carbon atoms, and $CO_2$. The keto-group of the intermediate is then reduced by the KCR to a hydroxyl-group. In the next step the DH cleaves of the hydroxyl-group ($H_2O$ is produced), forming a acyl-2-en-CoA ester (delta-2-enoyl-CoA). In the final step the double bound at position 2, 3 is reduced by the ECR forming the elongated acyl-CoA ester (Buchanan, Gruissem, Jones (2000) Biochemistry & Molecular biology of plants, American Society of Plant Physiologists). In the studies underlying this invention, a natural occurring fusion of DH and ECR with superior catalytic activities and specificities towards LCPUFA has been provided.

More preferably, polynucleotides having a nucleic acid sequence as shown in SEQ ID NOs: 1 or 3 encoding polypeptides having amino acid sequences as shown in SEQ ID NOs: 2 or 4 or variants thereof, preferably, exhibit nECR activity.

A polynucleotide encoding a polypeptide having a nECR activity as specified above has been obtained in accordance with the present invention, preferably, from *Thalassiosira pseudonana* or *Phaeodactylum tricornutum*. However, orthologs, paralogs or other homologs may be identified from other species. Preferably, they are obtained from plants such as algae, for example *Isochrysis, Mantoniella, Ostreococcus* or *Crypthecodinium*, algae/diatoms such as *Phaeodactylum, Thalassiosira* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from Euteleostomi, Actinopterygii; Neopterygii; Teleostei; Euteleostei, Protacanthopterygii, Salmoniformes; Salmonidae or Oncorhynchus, more preferably, from the order of the Salmoniformes, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thallasiosira* or *Phaeodactylum.*

Thus, the term "polynucleotide " as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins, Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 1 or 3 or by a polynucleotide encoding a polypeptide having an amino acid sequence as shown in any one of SEQ ID NOs: 2 or 4 by at least one nucleotide substitution, addition and/or deletion, whereby the variant nucleic acid sequence shall still encode a polypeptide having a nECR activity as specified above. Variants also encompass polynucleotides comprising a nucleic acid sequence Which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6,3 ,1-6.3,6, A preferred example for stringent hybridization conditions are hybridization conditions in 6 x sodium chloride/sodium citrate (=SSC) at approximately 45° C., followed by one or more wash steps in 0.2 ×SSC, 0 ,1% SDS at 50 to 65° C. The skilled worker knows that. these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5 ×SSC (pH 7.2), If organic solvent is present in the abovementioned. buffer, for example 50% formamide, the temperature under standard conditions is approximately 42° C. The hybridization conditions for DNA: DNA hybrids are, preferably, 0 ,1×SSC and 20° C. to 45 ° C., preferably between 30 ° C. , and 45° C. The hybridization conditions for DNA :RNA hybrids are, preferably, 0,1×SSC and 30° C. to 55° C. preferably between 45 ° and 55 °C. The abovementioned hybridization temperatures are determined for example for a nucleic acid with approximately 100 bp (=base pairs) in length and a G =C content of 50m% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i,e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples, As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 756%, at least 80%, at least 85%, at least 90%, at least 95%, at least 98% or at least 99% identical to the nucleic acid sequences shown in any one of SEQ 1 D NOs: 1 or 3 , preferably, encoding polypeptides retaining a ECR activity as specified above. Moreover, also encompassed are polynucleotides which comprise nucleic acid sequences encoding a polypeptide having an amino acid sequences which are at least 50%, at least 55%, at least 60%, at least 65%, at least 70% , at least 75%, at least 80%, at least 85%, at least 90%, at least 95%, at least 98% or at least 99% identical to the amino acid sequences shown in any one of SEQ ID NOs: 2 or 4, wherein the polypeptide, preferably, retains nECR activity as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice,P., Longden,I., and Bleasby,A, Trends in Genetics 1.6(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap extension penalty of 0.5, 1, 2, 3, 4, 5, or 6. Guides for local installation of the EMBOSS package as well as links to WEB-Services can be found at emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (EMBOSS: The European Molecular Biology Open Software Suite, Rice,P., Longden, I., and Bleasby,A, Trends in Genetics 16(6), 276-277 2000), using the EDNAFULL scoring matrix and a gap opening penalty of 16, 14, 12, 10, 8, 6, or 4 and a gap extension penalty of 0.5,1, 2, 3, 4, 5, or 6. A preferred, non-limiting example of parameters to be used in conjunction for aligning two sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2,2) of Altschul et al. (Altschul 1990, J. Mol , Biala 215:403-40). BLAST using nECR nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to nECR sequences of the invention. BLAST using nECR protein sequences of the invention as query sequence can be performed with the BLASTp or the tBLASTn program using default parameters to obtain either amino acid sequences (BLASTp) or nucleic acid sequences (tBLASTn) homologous to nECR sequences of the invention. To obtain gapped alignments for comparison purposes, Gapped BLAST using default parameters can be utilized as described in Altschul et al, (Altschul 1997, Nucleic Acids Res. 25(17 ):3389-3402).

TABLE 1

Relation of sequence types of querry- and hit-sequences for various BLAST programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragment shall encode a polypeptide which still has nECR activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining nECR activity to a significant extent, preferably, at least 10%, at least 20%, at least 30%, at least 40%, at least 50%, at least 60%, at least 70%, at least 80% or at least 90% of the nECR activity exhibited by any of the polypeptide shown in any one of SEQ ID NOs: 2 or 4. The activity may be tested as described in the accompanying Examples.

The polynucleotides of the present invention either essentially consist of the aforementioned nucleic acid sequences or comprise the aforementioned nucleic acid sequences. Thus, they may contain further nucleic acid sequences as well.

Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interfering with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

In the studies underlying the present invention, advantageously, polynucleotides where identified encoding dehydrateses from *Thalassiosira pseudonana* and *Phaeodactylum tricornumtum*. In particular, the *Thalassiosira pseudonana* and *Phaeodactylum* dehydratase/enoyl-CoA-reductase nECR have been identified [nECR(Tp) and nECR(Pt)]. Each of these nECR are capable of removing a hydroxyl group from 3-hydroxy-acyl-CoA and reducing the formed double bond as part of the elongation process for fatty acids. For example, the expression of the nECR(Tp) and nECR(Pt) in a *Saccharomyces cerevisae* mutant not been able to elongate fatty acids has been found to restore the elongation process. The polynucleotides of the present invention are particularly suitable for the recombinant manufacture of LCPUFAs and, in particular, ARA, EPA and/or DHA.

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, Ipp, Iac, Ipp-Iac, IacIq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from Glycine max (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5' end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 by or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed. The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site- directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, 2$^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, Agrobacterium protocols, Ed.: Gartland and Davey, Humana Press, Totowa, New Jersey. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the Agrobacterium-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in E. coli and in Agrobacterium. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Florida), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-Iac fusion promoter by host RNA polymerase. The target gene expression from the pET 11d vector is based on the transcription of a T7-gn10-Iac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the IacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell Biol. 3:2156-2165) and the pVL series (Lucklow 1989, Virology 170:31-39).

The polynucleotide of the present invention can be expressed in single-cell plant cells (such as algae), see Falciatore 1999, Marine Biotechnology 1 (3):239-251 and the references cited therein, and plant cells from higher plants (for example *Spermatophytes*, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the sorghum kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia*, and, *Schizochytrium.*

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

Generally, the controlling steps in the production of LCPUFAs, i.e., the long chain unsaturated fatty acid biosynthetic pathway, are catalyzed by membrane-associated fatty acid elongase complexes. Plants and most other eukaryotic organisms have specialized elongase system for the extension of fatty acids beyond C18 atoms. These elongase reactions have several important features in common with the fatty acid synthase complex (FAS). However, the elongase complex is different from the FAS complex as the complex is localized in the cytosol and are membrane bound, ACP is not involved and the elongase 3-keto-acyl-CoA-synthase catalyzes the condensation of malonyl-CoA with an acyl primer. The elongase complex consists of four components with different catalytic functions, the keto-acyl-CoA-synthase (KCS, condensation reaction of malonyl-CoA to acyl-CoA, creation of a 2 C atom longer keto-acyl-CoA fatty acid), the keto-acyl-CoA-reductase (KCR, reduction of the 3-keto group to a 3-hydroxy-group), the dehydratase (DH, dehydration results in a delta-2-enoyl-acyl-CoA fatty acid) and the enoly-CoA-reductase (ECR, reduction of the double bond at position 2, release from the complex). For the production of LCPUFAs including ARA, EPA and/or DHA the elongation reaction could be essential. Higher plants do not have the necessary enzyme set to produce LCPUFAs (4 or more double bonds, 20 or more C atoms). Therefore the catalytic activities have to be conferred to the plants or plant cells. One critical step in the process of elongation is the dehydration and reduction reaction. The polynucleotides of the present invention surprisingly catalyze the dehydration and reduction activity by one enzyme. By delivering this nECR increased levels of PUFAs and LCPUFAs are produced.

However, it will be understood that dependent on the host cell, further, enzymatic activities may be conferred to the host cells, e.g., by recombinant technologies. Accordingly, the present invention, preferably, envisages a host cell which in addition to the polynucleotide of the present invention comprises polynucleotides encoding such desaturases and/or elongases as required depending on the selected host cell. Preferred desaturases and/or elongases which shall be present in the host cell are at least one enzyme selected from the group consisting of: Δ-4-desaturase, Δ-5-desaturase, Δ-5-elongase, Δ-6-desaturase, Δ12-desaturase, Δ15-desaturase, ω3-desaturase and Δ-6-elongase. Especially preferred are the bifunctional d12d15-desaturases d12d15Des(Ac) from *Acanthamoeba castellanii* (WO2007042510), d12d15Des(Cp) from *Claviceps purpurea* (WO2008006202) and d12d15Des (Lg)1 from *Lottia gigantea* (WO2009016202), the d12-desaturases d12Des(Co) from *Calendula officinalis* (WO200185968), d12Des(Lb) from *Laccaria bicolor* (WO2009016202), d12Des(Mb) from *Monosiga brevicollis* (WO2009016202), dl2Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), dl2Des(Ps) from *Phytophthora sojae* (WO2006100241) and d12Des(Tp) from *Thalassiosira pseudonana* (WO2006069710), the d15-desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-desaturases d5Des(Ol)2 from *Ostreococcus lucimarinus* (WO2008040787), d5Des (Pp) from *Physcomitrella patens* (WO2004057001), d5Des (Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-desaturases d6Des(Cp) from *Ceratodon purpureus* (WO2000075341), d6Des(Ol) from *Ostreococcus lucimarinus* (WO2008040787), d6Des(Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6EIo(Om)2 from *Oncorhynchus mykiss* (WO2005012316), d5d6EIo(Ta) from *Thraustochytrium aureum* (WO2005012316) and d5d6EIo(Tc) from *Thraustochytrium* sp. (WO2005012316), the d5-elongases d5EIo (At) from *Arabidopsis thaliana* (WO2005012316), d5EIo (At)2 from *Arabidopsis thaliana* (WO2005012316), d5EIo (Ci) from *Ciona intestinalis* (WO2005012316), d5EIo(Ol) from *Ostreococcus lucimarinus* (WO2008040787), d5EIo (Ot) from *Ostreococcus tauri* (WO2005012316), d5EIo(Tp) from *Thalassiosira pseudonana* (WO2005012316) and d5EIo(Xl) from *Xenopus laevis* (WO2005012316), the d6-elongases d6EIo(Ol) from *Ostreococcus lucimarinus* (WO2008040787), d6EIo(Ot) from *Ostreococcus tauri* (WO2005012316), d6EIo(Pi) from *Phytophthora infestans* (WO2003064638), d6EIo(Pir) from *Pythium irregulare* (WO2009016208), d6EIo(Pp) from *Physcomitrella patens* (WO2001059128), d6EIo(Ps) from *Phytophthora sojae* (WO2006100241), d6EIo(Ps)2 from *Phytophthora sojae* (WO2006100241), d6Elo(Ps)3 from *Phytophthora sojae* (WO2006100241), d6EIo(Pt) from *Phaeodactylum tricornutum* (WO2005012316), d6EIo(Tc) from *Thraustochytrium* sp. (WO2005012316) and d6EIo(Tp) from *Thalassiosira pseudonana* (WO2005012316), the d9-elongases d9EIo(Ig) from *Isochrysis galbana* (WO2002077213), d9EIo(Pm) from *Perkinsus marinus* (WO2007093776) and d9EIo(Ro) from *Rhizopus oryzae* (WO2009016208). Particularly, if the manufuacture of ARA is envisaged in higher plants, the enzymes recited in Table 3, below (i.e. additionally a d6-desaturase, d6-elongase, d5-elongase, d5-desaturase, d12-desaturase, and d6-elongase) or enzymes having essentially the same activity may be combined in a host cell. If the manufacture of EPA is envisaged in higher plants, the enzymes recited in Table 4, below (i.e. additionally a d6-desaturase, d6-elongase, d5-desaturase, d12-desaturase, d6-elongase, omega 3-desaturase and d15-desaturase), or enzymes having essentially the same activity may be combined in a host cell. If the manufacture of DHA is envisaged in higher plants, the enzymes recited in Table 5, below (i.e. additionally a d6-desaturase, d6-elongase, d5-desaturase, d12-desaturase, d6-elongase, omega 3-desaturase, d15-desaturase, d5-elongase, and d4-desaturase), or enzymes having essentially the same activity may be combined in a host cell.

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore pertains to a method for the manufacture of a polypeptide encoded by a polynucleotide of any the present invention comprising a) cultivating the host cell of the invention under conditions which allow for the production of the said polypeptide; and b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention encompasses a polypeptide encoded by the polynucleotide of of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention. referred to above. Moreover, it includes chemically modified polypeptides. Such modifications may be artificial modifications or naturally occurring modifications such as phosphorylation, glycosylation, myristylation and the like (Review in Mann 2003, Nat, Biotechnol. 21, 255-261, review with focus on plants in Huber 2004, Curs, Opin. Plant Biol, 7, 318-322), Currently, more than 300 posttranslational modifications are known (see full ABM: Delta mass list at abrf.org/idex.cfm/dm.home). The polypeptide of the present invention shall exhibit the n ECR activitiy referred to above.

Encompassed by the present invention is, furthermore, an antibody which specifically recognizes the polypeptide of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the present invention contemplates a non-human transgenic organism comprising the polynucleotide or the vector of the present invention.

Preferably, the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as Tagetes. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum var. tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense,*

*Physcomitrium cupuliferum, Physcomitrium drummondii, Physcomitrium eurystomum, Physcomitrium flexifolium, Physcomitrium hookeri, Physcomitrium hookeri* var. serratum, *Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum or Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum or Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao*[cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, macadamia, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes, Solanaceae* plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophtora infestans, Thallasiosira pseudonona* and *Cryptocodinium cohnii*.

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the Agrobacterium-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

However, it will be understood that dependent on the non-human transgenic organism specified above, further, enzymatic activities may be conferred to the said organism, e.g., by recombinant technologies. Accordingly, the present invention, preferably, envisages a non-human transgenic organism specified above which in addition to the polynucleotide of the present invention comprises polynucleotides encoding such desaturases and/or elongases as required depending on the selected host cell. Preferred desaturases and/or elongases which shall be present in the organism are at least one enzyme selected from the group of desaturases and/or elongases or the combinations specifically recited elsewhere in this specification (see above and Tables 3, 4 and 5).

Furthermore, the present invention encompasses a method for the manufacture of polyunsaturated fatty acids comprising:

a) cultivating the host cell of the invention under conditions which allow for the production of polyunsaturated fatty acids in said host cell; and
b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of DGLA 20:3 (8,11,14), ARA 20:4 (5,8,11,14), iARA 20:4(8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of ARA, EPA or DHA. Moreover, also encompassed are the intermediates of LCPUFA which occur during synthesis. Such intermediates are, preferably, formed from substrates by the nECR activity of the polypeptide of the present invention. Preferably, substrates encompass LA 18:2 (9,12), GLA 18:3 (6,9,12), DGLA 20:3 (8,11,14), ARA 20:4 (5,8,11,14), eicosadienoic acid 20:2 (11, 14), Eicosatetraenoic acid 20:4 (8,11,14,17), Eicosapentaenoic acid 20:5 (5,8,11,14,17).

The term "cultivating" as used herein refers maintaining and growing the host cells under culture conditions which allow the cells to produce the said polyunsaturated fatty acid, i.e. the PUFA and/or LCPUFA referred to above. This implies that the polynucleotide of the present invention is expressed in the host cell so that the nECR activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, ARA, EPA, DHA, in free or in —CoA bound form, as membrane phospholipids or as triacylglyceride estres. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere dependent on the type of organism. The pH of the liquid medium can either be kept constant, that is to say regulated during the culturing period, or not. The cultures can be grown batchwise, semibatchwise or continuously. Nutrients can be provided at the beginning of the fermentation or administered semicontinuously or continuously: The produced PUFA or LCPUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of poly-unsaturated fatty acids comprising:

a) cultivating the non-human transgenic organism of the invention under conditions which allow for the production of poly-unsaturated fatty acids in said host cell; and
b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or medicaments. Accordingly, the formulation of the PUFA or LCPUFA shall be carried out according to the GMP standards for the individual envisaged products. For example, an oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

The present invention also relates to an oil comprising a polyunsaturated fatty acid obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

The contents of all references cited throughout this application are herewith incorporated by reference in general and with respect to their specific disclosure content referred to above.

FIGURES

FIG. 1 shows the nucleotide (SEQ ID NO: 1) and amino acid sequences of nECR from *Thalassiosira pseudonana* (SEQ ID NO: 2).

FIG. 2 shows the nucleotide and amino acid sequence of nECR from *Phaeodactylum tricornutum* as follows: A) the cDNA sequence of the mRNA (SEQ ID NO:3); B) the translated amino acid sequence (SEQ ID NO:4)

Figure 3:
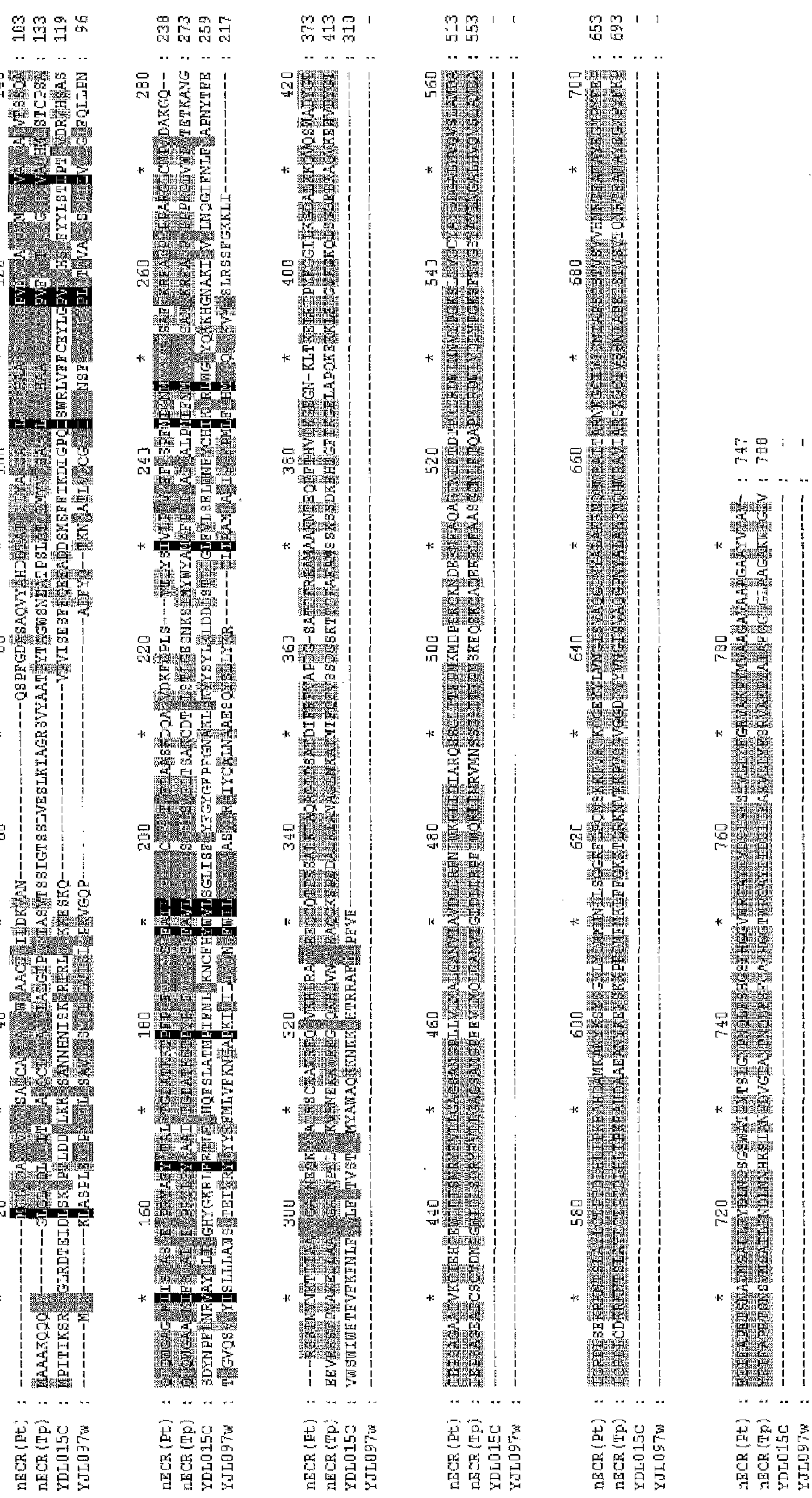
FIG. 3 shows an Alignment of the amino acid sequences from nECR from *T. pseudonana* and *P. tricornutum* with the dehydratase (YJL097W) and enoyl-CoA-reductase (YDL015C) from*Saccharomyces cerevisae*

FIG. 4 shows the similarity table of the aligment from FIG. 3. The identity table was done by ClustalW alignment using the Align program from the Vector NTI software package (Invitrogen). The two nECR from the different organisms share 65% identity whereas both nECR have below 30% identity to the known dehydratase (YJL097w) or enoyl-CoA-reductase (YDL015C) from yeast.

Figure 5:
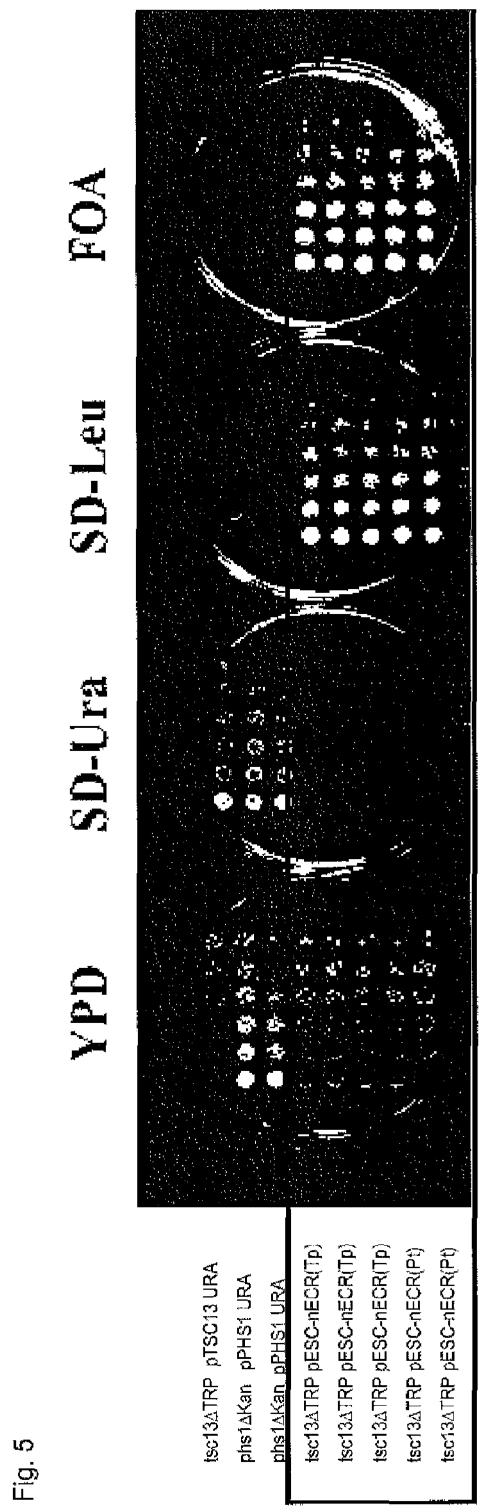

FIG. 5 shows the functional characterization of nECR(Tp) and nECR(Pt) by yeast complementation assay. The complementation assay was performed with nECR(Tp) and nECR (Pt) in yeast Δydl015c, which has no functional enoyl-CoA-reductase. Legend: YPD, complete medium, SD-Ura, medium lacking uracil, SD-Leu, medium lacking leucine, FOA, medium containing leucine and 5-FOA; (1)tsc13ΔTrp pTSC13 URA: yeast mutant Δydl015C lacking the function of the enoyl-CoA-reductase, transformed with the vector pTSC13 containing the functional YDL015C gene; (2) phs1Δκan pPHS1 URA: yeast mutant Δyjl097w lacking the function of the dehydratase, transformed with the vector pPHS1 containing the functional YJL097W gene; (3) tsc13ΔTrp pESC-nECR(Tp): yeast mutant Δydl015C lacking the function of the enoyl-CoA-reductase, transformed with the vector pESC-nECR(Tp); (4) sc13ΔTrp pESC-nECR(Pt): yeast mutant Δydl015C lacking the function of the enoyl-CoA-reductase, transformed with the vector pESC-nECR(Pt)

Figure 6:
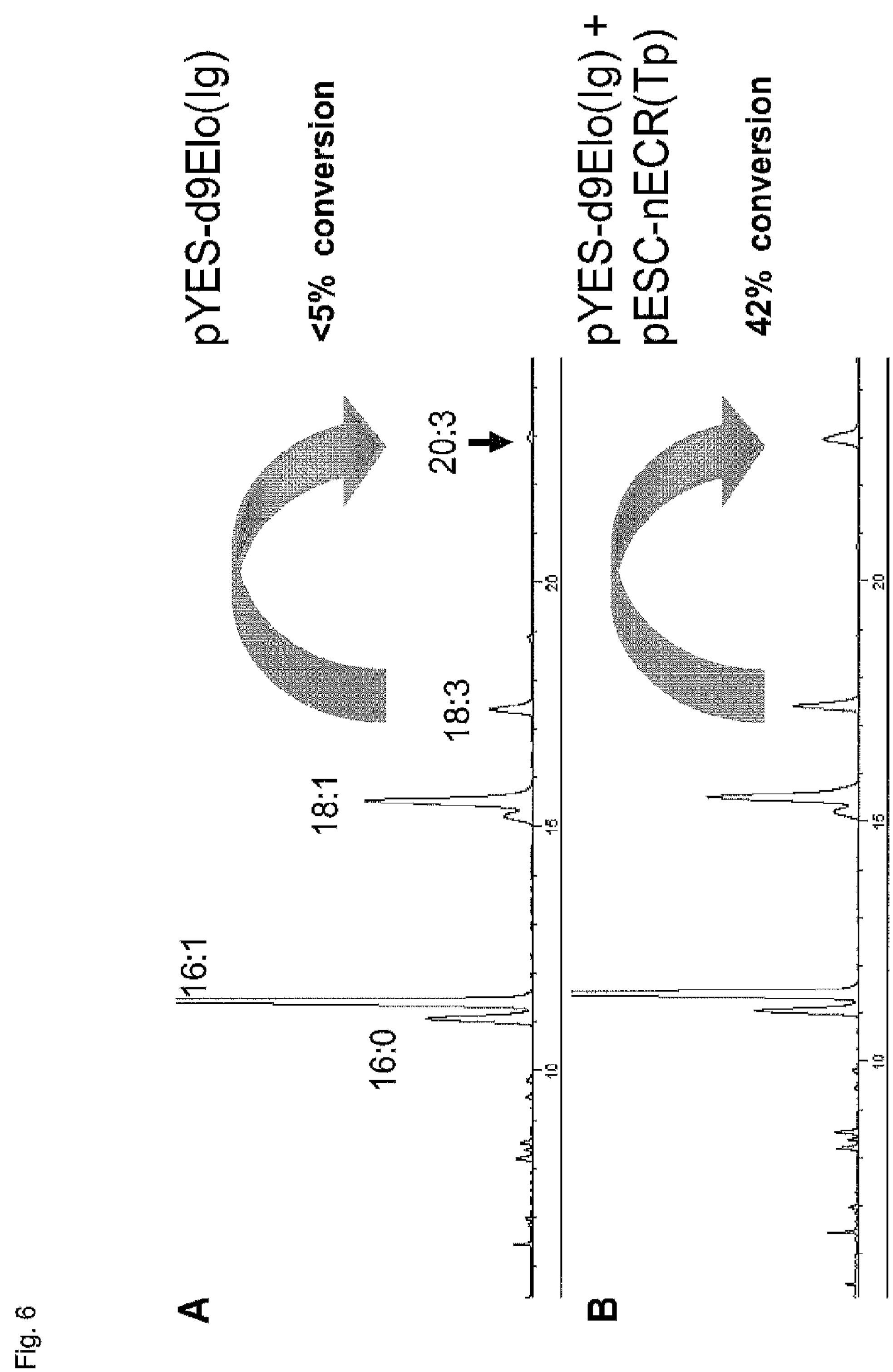

FIG. 6 shows the increased production of long-chain PUFA with nECR(Tp). Increased production of long-chain PUFA with nECR(Tp). Yeast transformed with pYES-d9EIo(Ig) (A) or pYES-d9EIo(Ig)+pESC-nECR(Tp) (B) were fed with 25 μM linolenic acid (18:3Δ9,12,15) in the SD(-Ura-Leu) medium. After 48 h of incubation the yeast cells were centrifuged and the pellets subjected to gas chromatographic analysis. The gas chromatographs show the different fatty acids in the two different yeast strains without (A) and with nECR (Tp) (B). Conversion rates are figured as following: (product/substrate-product)*100.

Figure 7:
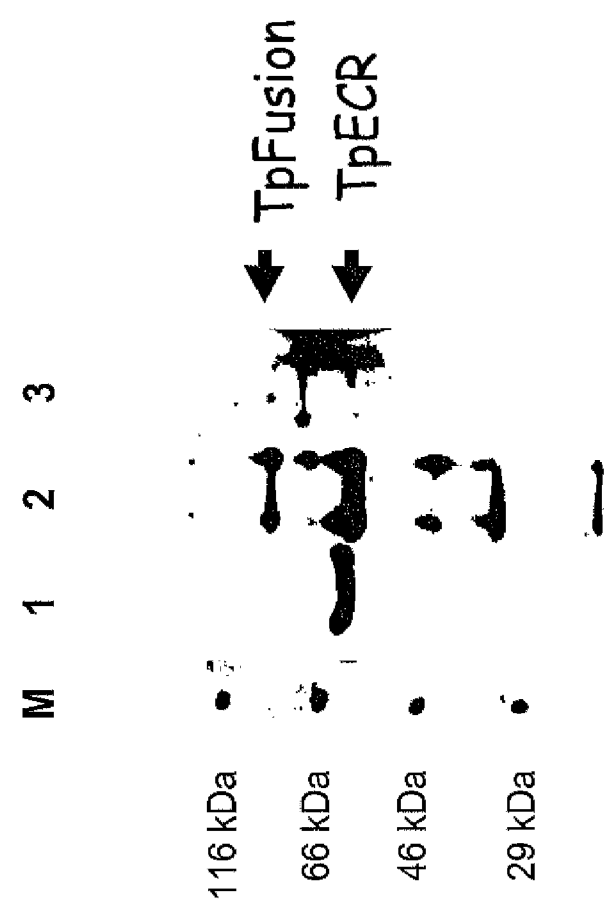

FIG. 7 shows a Western Blot analysis of *T. pseudonana* subcellular fractions. M, protein size marker, 1, total extract, 2, soluble fraction, 3, membrane fraction. The arrows indicate the two versions of nECR(Tp).

Figure 8:
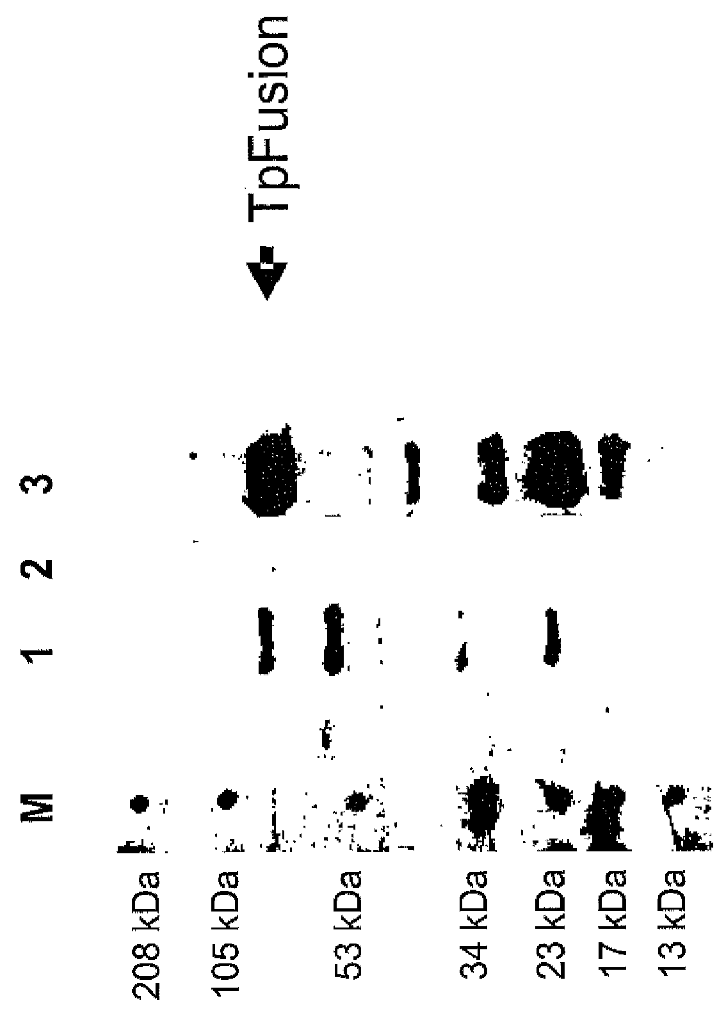

FIG. 8 shows a Western Blot analysis of subcellular fractions from yeast expressing nECR(Tp). M, protein size marker, 1, total extract, 2, soluble fraction, 3, membrane fraction. The arrow indicates the nECR(Tp) fusion protein.

Figure 9:
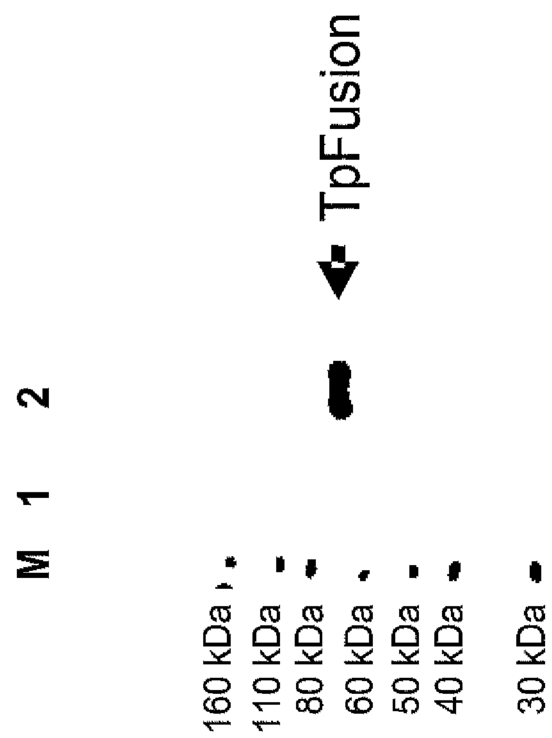

FIG. 9 shows a Western Blot analysis of subcellular fractions from yeast expressing nECR(Tp). M, protein size marker, 1, total extract, 2, soluble fraction, 3, membrane fraction. The arrow indicates the nECR(Tp) fusion protein.

This invention is further illustrated by the following examples which should not be construed as limiting. The contents of all references, patents and published patent applications cited throughout this application, as well as the figures, are incorporated herein by reference.

EXAMPLES

Example 1

Organisms and Culture Conditions

For regeneration of haploids, the method outlined in Pan et al 2004 (Molecular Cell 16:487-496) was used. Briefly, cultures were grown overnight in DOB-uracil, then approximately 25 $OD_{600}$ of each culture was washed and resuspended in fresh media and grown for 3 hours. Cells were then suspended in sporulation media (1% potassium acetate, 0.005% zinc acetate), sporulated for 5 days and spread on haploid selection magic media plates (2% galactose, amino acid mix—uracil-leucine-histidine-arginine, 0.17% nitrogen base without amino acids or ammonium sulfate, 0.1% sodium glutamate) containing 200 mg/L G418 and 60 mg/L canavanine.

Example 2

Novel Dehydratase/Enoyl-CoA-Reducatase Sequences

PUFA producing algae were screened to reveal differences between non-PUFA producers. Sequences from *Thalassiosira* and *Phaeodactylum* were obtained, which are specific for these PUFA producers (FIGS. 1 and 2). Alignment with known dehydratase and enoyl-CoA-reductase sequences from yeast (YJL097W and YDL015C) showed low homology (FIGS. 3 and 4). Therefore the newly generated nECR represents a novel class of enzymes. By complementation assays (Example 3) the sequences exhibit dehydratase and enoyl-CoA-reducatase activity and were therefore termed nECR.

A list of identified full-length coding sequences is shown in Table 1a and 1b.

TABLE 1a

List of full-length coding sequences

| SEQ ID NO: | Gene | Organism | Length in bp |
|---|---|---|---|
| 1 | nECR(Tp) | *Thalassiosira pseudonana* | 2367 |
| 3 | nECR(Pt) | *Phaeodactylum tricornutum* | 2244 |

TABLE 1b

List of deduced amino acids from sequences described in Table 1,

| SEQ ID NO: | Gene | Organism | Length in amino acids |
|---|---|---|---|
| 2 | nECR(Tp) | *Thalassiosira pseudonana* | 788 |
| 4 | nECR(Pt) | *Phaeodactylum tricornutum* | 747 |

Open reading frames as shown in Table 1 were cloned into the pESC(Leu) vector from Stratagene according to manufactures reaction conditions. Reactions were transformed into *E. coli* DH5α and plasmid DNA was isolated. The plasmids pESC-nECR(Tp), pESC-nECR(Pt) were then used for yeast transformation. As both mutant yeast strains Δydl015C (Δtsc13) and Δyjl097w (Δphs1) are lethal, the strains have been transformed with plasmids complementing the mutant with uracil-auxothropie marker URA (pTSC13 and pPHS1). Vectors containing the URA marker can be removed in yeast by using 5-FOA (5-fluoroorotic acid; Sadowski et al. Yeast. 2008 Aug; 25 (8):595-9).

Example 3

Yeast Transformation and Growth Conditions

*S. cerevisiae* strain YSC1021-674054 from Open Biosystems was transformed with the constructs pESC-nECR(Tp), pESC-nECR(Pt) and pESC using the S. C. EasyComp Transformation Kit (Invitrogen, Carlsbad, California) with selection on leucine-deficient medium. For assessing the dehydratase/enoyl-CoA-reductase activity complementation studies were done. For that purpose the heterozygous magic marker strain YSC1021-674054 from Open Biosystems was used. This strain does not exhibit any enoyl-CoA-reductase activity. As the enoyl-CoA-reductase activity delivers elongated fatty acids and these fatty acids are required for cell growth and division, the respective yeast strain will not grow on medium not containing said elongated fatty acids.

Following Transformats were Generated:

1. tsc13ΔTrp pTSC13 URA: yeast mutant Δydl015C lacking the function of the enoyl-CoA-reductase, transformed with the vector pTSC13 containing the functional YDL015C gene.
2. phs1Δκan pPHS1 URA: yeast mutant Δyjl097w lacking the function of the dehydratase, transformed with the vector pPHS1 containing the functional YJL097W gene.
3. tsc13ΔTrp pESC-nECR(Tp): yeast mutant Δydl015C lacking the function of the enoyl-CoA-reductase, transformed with the vector pESC-nECR(Tp)
4. sc13ΔTrp pESC-nECR(Pt): yeast mutant Δydl015C lacking the function of the enoyl-CoA-reductase, transformed with the vector pESC-nECR(Pt)

Yeast were grown after transformation in complete medium containing all amino acids and nucleotides. Then yeast were plated on different medium containing either the complete medium (SD), the complete medium lacking uracil (SD-Ura), the complete medium lacking leucine (SD-Leu) or the complete medium lacking leucine and containing 5-FOA (FIG. 5). Plasmids 1 and 2 can grow on SD and SD-Ura, but not on SD-Leu as they are not having the LEU marker. Plasmids 3 and 4 can grow on SD and SD-Leu, but not on SD-Ura as they are missing the URA marker. The complementation is shown on plates containing FOA, which removes plasmids with the URA marker (1 and 2). However, even in the absence of plasmids 1 or 2 there is growth of colonies with plasmids 3 and 4 (FIG. 5, FOA).

Therefore both sequences nECR(Tp) and nECR(Pt) are capable of complementing the lethal null mutation in the yeast 3-hydroxy acyl-CoA dehydratase gene Δydl015C.

In summary, by complementation of a defective yeast mutant it could been shown that the sequences nECR(Tp) and nECR(Pt) are biological functional and exhibit enoyl-CoA-reductase activity.

Example 4

Expression of nECR(Tp) in Combination with the d9-elongase from *Isochrysis galbana*

To examine the utility of nECR(Tp) in the production of polyunsaturated fatty acids in plants, for example, for nutraceutical use, the gene was expressed in combination with a PUFA-elongase component, the d9-elongase from lsochrysis galbana (WO2002/077213). This enzyme catalyzes the elongation of linoleic or linolenic acid (18:2Δ9,12 or 18:3Δ9,12,15). The aim of the experiment was to analyze, if the addition of nECR(Tp) increases the productivity of the d9-elongase from *I. galbana*. For that purpose yeast cells (INVSC from Invitrogen) transformed with pESC-nECR(Tp) and grown on DOB(-leucine) plates were further transformed with the plasmid pYES(Ura)-d9EIo(Ig) as described in Example 1 and grown on DOB(-uracil, -leucine). The vector pYES(Ura) was derived from Invitrogene and mediates auxotrophy for uracil. The open reading frame of d9EIo(Ig) as described in WO2002/077213 was cloned into pYES2 according to manufactures conditions. As a control experiment pYES-d9EIo(Ig) was transformed into the control yeast strain containing only the pYES vector.

Surprisingly a difference in the amount of the elongation product 20:3 between the control (pESC-d9EIo(Ig) and the yeast containing two components of the elongation complex (pESC-d9EIo(Ig)+pYES-nECR(Tp) was observed.

In FIG. 6 it is shown that the addition of the nECR(Tp) gene has an tremendous influence on the productivity of long-chain PUFA. Productivity was increased 8-fold compared to the control experiment. The productivity is measured in the conversion of the substrate 18:3 (exogenously added to the yeast medium) to the elongated PUFA fatty acid 20:3.

In summary nECR improves greatly the production of elongated fatty acids, such as long-chain PUFA beneficial for human health.

Example 5

Comparison of Yeast Expressed nECR(Tp) and the Native Protein from *T. pseudonana*

Antibodies against nECR(Tp) have been produced according to manufactures practice (Eurogentec, Belgium; peptide antibody). The antibodies are highly specific for nECR(Tp) in *T. pseudonana* and the heterologous expression in yeast (FIG. 7 and FIG. 8). With the use of the antibodies structural differences between the natural organism and the heterologous expression could be observed (FIG. 7 and FIG. 8).

Western Blot experiments were Done Using Standard Protocols:

SDS-PAGE was done according to Laemmli (1970) with precast gels from Biorad. As loading buffer 0.05 M Tris/HCl pH6.8, 0.1 M DTT, 2% (w/v) SDS, 0.1% Bromphenolic blue and 10% Glycerol was used. SDS-PAGE gels were then blotted on nitrocellulose using a Protean BA85 nitrocellulose membrane (Schleicher&Schuell). Transfers on the membranes were done with a buffer containing 15 mM $Na_2HPO_4$ pH7.2, 0.05% (w/v) SDS, 20% (v/v) Methanol for 2 h at 200 mA, 40 V (Protean II, Biorad). For the immunological test the membrane was blocked for 1 h in PBS (0.14M NaCl, 2.7 mM KCl, 10 mM $Na_2HPO_4$, 1.8 mM $KH_2PO_4$ pH7.4), 5% (w/v) milk powder. The serum containing the antibodies against nECR(Tp) was added at a concentration of 1:2000 and incubated overnight at 4° C. For detection of the antibodies the membrane was washed three times with PBS and blocked again with PBS, 5% (w/v) milk powder for 30 min. One unit of secondary antibody (Biorad anti-rabbit horse radish peroxidase) was added and further incubated for 30 min. After three times washing with PBS the membrane was immersed in ECL solution and 1 min incubated. Then the solution was removed with a paper tissue and the membrane was wrapped with Saran. Detection of the chemiluminiscence was done in the Biollluminator (LKB).

For protein isolation from *T. pseudonana*, a culture of 500 mL was incubated for 14 days at 20° C. in F2 medium (growth conditions and media for *T. pseudonana* used as described in Tonon et al. (Tono 2005, FEBS J. 272:3401-3412). The algae was harvested by centrifucation (10 min, 5000× g) and the pellet was put into a mortar. Using a pistil a fine powder was generated. The powder was suspended with 50 mM Tris/HCl pH 8.0, 2 mM EDTA and filtered through 2 layers of Miracloth (Merck) or any other filter membrane. The filter product was then aliquoted and aliquots of 50 uL were mixed with SDS-PAGE loading buffer (see above).

Analysis of the nECR(Tp) detected by Western Blot in *T. pseudonana* (FIG. 7) showed that the protein of nECR(Tp) can be found in the cell debris, soluble and membrane fraction. Surprisingly in *T. pseudonana* the major form is a cleaved version which contains only the enoyl-CoA reductase activity (ECR). The proof for the ECR domain is deduced from the location of the binding site of the antibodies in the ECR domain. The larger fusion protein of nECR(Tp) is found only in small quantities in the soluble fraction. No nECR(Tp) could be found in the membrane fraction, even after longer exposure times.

Therefore it can be concluded that in *T. pseudonana* there are two versions of nECR(Tp), the protein as deduced from the cDNA (SEQ ID NO 1) and a post-translationally modified shorter version containing only the ECR domain. Only the ECR domain is membrane bound and therefore correctly localized (functionality of ECR in the elongase complex takes place at the microsomal membranes (Napier 2007, Annu Rev Plant Biol 58:295-319)).

With the heterologous expression of nECR(Tp) in yeast a different picture can be observed. As described in Example 4 yeast with pESC-nECR(Tp) was used for protein extraction. Yeast was grown for 3 d at 28° C. in 50 ml cultures and pellets were harvested by centrifugation (10 min, 5000× g). The pellet was aliquoted, frozen with liquid nitrogen and a steel bead added compatible with the Qiagen/Tresch mill system. Pellets were subjected to 5 min in the Tresch mill for cell disruption. Total cell extracts were separated in soluble and membrane fraction by a 30 min 100,000×g centrifugation step. The pellet constitutes the membrane fraction, the supernatant the soluble one. All three fractions were subjected to SDS-PAGE and Western analysis as described above and analyzed (FIG. 8). In yeast no cleavage of nECR(Tp) could be observed. From the molecular weight the yeast expressed fusion protein runs at approx. 86 kDa which is comparable to nECR(Tp) in *T. pseudonana*. No 59 kDa ECR cleaved version is present. Therefore it can be concluded that nECR(Tp) as it complements the yeast KO mutants (Example 3) is fully functional in it's uncleaved form, thereby representing a new class of proteins. Further, the soluble and microsomal fractions were analyzed in detail to check if there is any soluble fraction of nECR(Tp) (FIG. 9). Again supernatant and microsomal fraction was loaded on a gel and exposed for a longer time. No nECR(Tp) could be found in the soluble fraction, again showing a structural difference to the native version from *T. pseudonana*.

In conclusion a new fusion protein was discovered which surprisingly contains two enzyme activities of the elongation complex (ECR and DH). SEQ ID NO. 1 results in the expression in heterologous systems in a functional fusion protein, which has different structural properties than the native proteins in *T. pseudonana.*

Example 6

Expression of nECR(Tp) and nECR(Pt) in Plants

The novel nECR from *T. pseudonana* and *P. tricornutum* are cloned into a plant transformation vector as described in WO2003/093482, WO20051083093 or WO2007/093776. Exemplary suitable combinations of genes are described in Table 3, 4 and 5.

TABLE 3

Gene combinations for the production of ARA.

| Gene | Aktivität | SEQ ID NO: |
|---|---|---|
| D6Des(Ot) | Δ6-Desaturase | 5 |
| D6Elo(Pp) | Δ6-Elongase | 6 |
| D5Des(Tc) | Δ5-Desaturase | 7 |
| D12Des(Ps) | Δ12-Desaturase | 8 |
| D6Elo(Tp) | Δ6-Elongase | 9 |
| nECR(Tp) or nECR(Pt) | nECR | 1 or 3 |

TABLE 4

Gene combinations for the production of EPA.

| Gene | Aktivität | SEQ ID NO: |
|---|---|---|
| D6Des(Ot) | Δ6-Desaturase | 5 |
| D6Elo(Pp) | Δ6-Elongase | 6 |
| D5Des(Tc) | Δ5-Desaturase | 7 |
| D12Des(Ps) | Δ12-Desaturase | 8 |
| D6Elo(Tp) | Δ6-Elongase | 9 |
| (3-Des(Pi) | Omega 3-Desaturase | 10 |
| D15Des(Cp) | Δ15-Desaturase | 11 |
| nECR(Tp) or nECR(Pt) | nECR | 1 or 3 |

TABLE 5

Gene combinations for the production of DHA.

| Gene | Aktivität | SEQ ID NO: |
|---|---|---|
| D6Des(Ot) | Δ6-Desaturase | 5 |
| D6Elo(Pp) | Δ6-Elongase | 6 |
| D5Des(Tc) | Δ5-Desaturase | 7 |
| D12Des(Ps) | Δ12-Desaturase | 8 |
| D6Elo(Tp) | Δ6-Elongase | 9 |
| ω3-Des(Pi) | Omega 3-Desaturase | 10 |
| D15Des(Cp) | Δ15-Desaturase | 11 |
| D5Elo(Ot) | Δ5-elongase | 12 |
| D4Des(Tc) | Δ4-desaturase | 13 |
| nECR(Tp) or nECR(Pt) | nECR | 1 or 3 |

Transgenic rapeseed lines are generated as described in Deblaere et al, 1984, Nucl. Acids. Res. 13, 4777-4788 and seeds of transgenic rapeseed plants are analyzed as described in Qiu et al. 2001, J. Biol. Chem. 276, 31561-31566.

Reference List

Arondel, V., Lemieux, B., Hwang, I., Gibson, S., Goodman, H. M., and Somerville, C. R. (1992). Map-based cloning of a gene controlling omega-3 fatty acid desaturation in Arabidopsis. Science 258, 1353-1355.

Broadwater, J. A., Whittle, E., and Shanklin, J. (2002). Desaturation and hydroxylation. Residues 148 and 324 of Arabidopsis FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from *Mortierella alpina* by heterologous expression in Bakers' yeast and canola. J. Biol. Chem. 273, 29360-29366.

Mantle, P. G. and Nisbet, L. J. (1976). Differentiation of *Claviceps purpurea* in axenic culture. J. Gen. Microbial. 93, 321-334.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant Microbe Interact. 15, 303-312.

Okuley, J., Lightner, J., Feldmann, K., Yadav, N., Lark, E., and Browse, J. (1994). Arabidopsis FAD2 gene encodes the enzyme that is essential for polyunsaturated lipid synthesis. Plant Cell 6, 147-158.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745. Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641.

Tudzynski, P., Correia, T., and Keller, U. (2001). Biotechnology and genetics of ergot alkaloids. Appl. Microbial. Biotechnol. 57, 593-605.

All references cited in this specification are herewith incorporated by reference with respect to their entire disclosure content and the disclosure content specifically mentioned in this specification.

The invention claimed is:

1. A polynucleotide comprising an expression control sequence operatively linked to a heterologous nucleic acid sequence selected from the group consisting of:

a) the nucleic acid sequence of SEQ ID NO 1 or 3;

b) a nucleic acid sequence encoding a polypeptide comprising the amino acid sequence of SEQ ID NO: 2 or 4;

c) a nucleic acid sequence having at least 50% sequence identity to the nucleic acid sequence of a) or b), wherein said nucleic acid sequence encodes a polypeptide having fatty acid dehydratase/enoyl-CoA reductase (nECR) activity; and d) a nucleic acid sequence encoding a polypeptide having nECR activity and comprising an amino acid sequence having at least 50% sequence identity to the amino acid sequence of SEQ ID NO 2 or 4.

2. The polynucleotide of claim 1, wherein said polynucleotide further comprises a terminator sequence operatively linked to the nucleic acid sequence.

3. A vector comprising the polynucleotide of claim 1.

4. A host cell comprising the polynucleotide of claim 1.

5. A method for the manufacture of a polypeptide comprisirig:

a) cultivating a host cell comprising the polynucleotide of claim 1 under conditions which allow for the production of a polypeptide encoded by said nucleic acid sequence; and b) obtaining the polypeptide from the host cell of step a).

6. A non-human transgenic organism comprising the polynucleotide of claim 1, wherein said organism is a microoraanism, yeast, or plant.

7. A plant, plant part, or plant seed comprising the polynucleotide of claim 1.

8. A method for the manufacture of a polyunsaturated fatty acid comprising:

a) cultivating the host cell of claim 4 under conditions which allow for the production of polyunsaturated fatty acids in said host cell; and b) obtaining said polyunsaturated fatty acids from said host cell.

9. The method of claim 8, wherein said polyunsaturated fatty acid is arachidonic acid (ARA), eicosapentaenoic acid (EPA), or docosahexaenoic acid (DHA).

10. A method for the manufacture of an oil, lipid, or fatty acid composition comprising:

a) cultivating the host cell of claim 4 under conditions which allow for the production of polyunsaturated fatty acids in said host cell;

b) obtaining said polyunsaturated fatty acids from said host cell; and c) formulating the polyunsaturated tatty acid as an oil, lipid, or fatty acid composition.

11. The method of claim 10, wherein said oil, lipid, or fatty acid composition is used for feed, foodstuffs, cosmetics, or medicaments.

12. A method for the manufacture of a polyunsaturated fatty acid comprising:

a) cultivating the non-human transgenic organism of claim 6 under conditions which allow for the production of polyunsaturated fatty acids in said organism; and b) obtaining said polyunsaturated fatty acids from said non-human transgenic organism.

13. The method of claim 12, wherein the polyunsaturated fatty acid is arachidonic acid (ARA), eicosapentacnoic acid (EPA) or docosahexaenoic acid (DHA).

14. A method for the manufacture of an oil, lipid, or fatty acid composition comprising:

a) cultivating the non-human transgenic organism of claim 6 under conditions which allow for the production of polyunsaturated fatty acids in said organism;

b) obtaining said polyunsaturated fatty acids from said non-human transgenic organism;

c) formulating the polyunsaturated fatty acid as an oil, lipid, or fatty acid composition.

15. The method of claim 14, wherein said oil, lipid, or fatter acid composition is used for feed, foodstuffs, cosmetics, or medicaments.

16. A polynucleotide comprising an expression control sequence operatively linked to a heterologous nucleic acid sequence selected from the group consisting of:

a) the nucleic acid sequence of SEQ ID NO: 1 or 3;

b) a nucleic acid sequence encoding a polypeptide comprising the amino acid sequence of SEQ ID NO: 2 or 4; and c) a nucleic acid sequence encoding a polypeptide having at least 90% sequence identity to the amino acid sequence of SEQ ID NO: 2 or 4 and having nECR activity.

17. The polynucleotide of claim 16, wherein said nucleic acid sequence encodes a polypeptide having at least 95% sequence identity to the amino acid sequence of SEQ ID NO: 2 or 4 and having nECR activity.

* * * * *

SEQUENCE LISTING

<160> NUMBER OF SEQ ID NOS: 26

<210> SEQ ID NO 1
<211> LENGTH: 2367
<212> TYPE: DNA
<213> ORGANISM: Thalassiosira pseudonana

<400> SEQUENCE: 1

```
atggctgctg ctaaacaaca acagtctaag ggacttggac ttaaggatct ctaccttata     60
acttacaacg ctttgtgttg tcttggatgg gcttacgttc ttgctcttgg aatccctacc    120
tttatcgctt ctgtgacctc ttctatcgga acttctagcc ttgttgagtc tcttaagatc    180
gctggaagat ctgtttacgc tgctactcct tacactgctg gatggtctaa cgaggctact    240
ccttctcttg ctaccgttct tatgtacgtt cagtctgctg ctgttcttga gatcgttcac    300
gctgctcttg gacttgttag atctcctgtt ttcgtgacca ctatgcaagt tggatcaaga    360
atcgttgctc tccatatgct ttctacttgt ccttctgctc aaactcaatg ggagctgct     420
cttatgatct tctcttgggc tcttgttgaa gttcctcgtt acctcttcta cgttgctgct    480
atcgttactg gtgatgctac taagggaact ccttaccctt tgttctggct cagatactct    540
cttttcgctg ttctttaccc tactggaatc tctggtgagt tgtctgtttt cctcacttct    600
gctaagtgcg ataccttcct ttctaccctc ggtgaaagca acaagtctat tatgtactgg    660
tacgctatgg ctttccctat tatctacgct cctggtgctc tccctatgat cttcaatatg    720
gtggctaacc gtaagtctgc tatgaagaag agattcgcta gacctcctcc acctcctaga    780
ggacttgttt ggcctgttac tgagactaag gctaacggtg aagaagttag atcttctacc    840
cctgtggcta aagagatcct tgctgctgct atcggagctg ttaaccctga gcttgctgag    900
aaagtgagaa acgagaagaa gtggagattc ggataccaaa agcacctcgt gaatatggtt    960
gaggctcagt gtaagtctcc tgaggatgct cttaagattg ctaacgccgg acttaacaag   1020
gcttatatga ccttccagtt cgtttcttct gatggatcta agactactac tttcgctgag   1080
gctatgtcta gcaagtctag cgataagttc cacactggtt ttatcaaggg tgaactcgct   1140
cctcaaaaag agaagaagct cgaagttgga tacaagggaa agcagatctc tggtgatgag   1200
cttaaggctc aagtgaaaga gtgggttgac tacggaacta tcgagccttc tgctggtgaa   1260
gctatctgtt cttgcgttga taaccctgga tggatcgatc tttctgacag atacttcgtt   1320
cttcttggag ctggatctgc tatgggacct ttcgaggttt tgatgcaact tggagctaac   1380
gttatcggaa tcgacctcga cagacctttt atctggcaga ggcttatcaa cagagtgatg   1440
aactcttctg gatctatcac cttccctatg tctaaagaac agagcaagtg cgctgatgag   1500
aaagagcttt tcgctgcttc tggatgcaac cttttcactc aggctcctat gatcagagat   1560
tggctcgttg atctttaccc tggaaagtct ttcactgtgg gatcttacgc ttaccttaac   1620
ggtgctctcc acgttcaagt ttctcttgct atggatgcta tctgtcgtga tctctgcgat   1680
aagaggaaga acacttctct tgcttacctc tgcactccta ctgatcttca ccttatccct   1740
aaagaggctc acgacgctgc tgaggctaac tacaaagagt tcagcaagaa acctttctgt   1800
atgtttatga agttgttctt cggaaagaaa accctcagaa agaacgtgaa gaagcctgtt   1860
agcggagttg gtggagattt ctactacgtg aacggaatct ctgttgctca aggacctaac   1920
tacgctcttg ctaagagaat gcaacactgg cgtgctgtta tcgctagaag caagggatgt   1980
atcgtgtcta gcaatatcgc tccttctacc tctactgttt ctgtgactca gaacagaact   2040
ttcgcttggg cttacgaggg aatgccttac ttcaagcctt acgagatctt cgctcctgag   2100
acttctaact ctgtgatgag cgctatcctt ttcaacgatc tcaacaacca caagtctatc   2160
gctaaccctg atgttggaat cgctaaccca aaccagcttt tctctttcgg tgctttccac   2220
ggtggaactt ggagatgtgc ttacgagatt gattctatcg gagaggcttc tgttcttctc   2280
tacttctctc gtgttgctaa accttacgct atcgctttcg gaggacttgg tctagctgct   2340
```

```
ggtgctaagt ggttcggaat tgtgtga                                   2367


<210> SEQ ID NO 2
<211> LENGTH: 788
<212> TYPE: PRT
<213> ORGANISM: Thalassiosira pseudonana

<400> SEQUENCE: 2

Met Ala Ala Ala Lys Gln Gln Gln Ser Lys Gly Leu Gly Leu Lys Asp
1               5                   10                  15

Leu Tyr Leu Ile Thr Tyr Asn Ala Leu Cys Cys Leu Gly Trp Ala Tyr
            20                  25                  30

Val Leu Ala Leu Gly Ile Pro Thr Phe Ile Ala Ser Val Thr Ser Ser
        35                  40                  45

Ile Gly Thr Ser Ser Leu Val Glu Ser Leu Lys Ile Ala Gly Arg Ser
    50                  55                  60

Val Tyr Ala Ala Thr Pro Tyr Thr Ala Gly Trp Ser Asn Glu Ala Thr
65                  70                  75                  80

Pro Ser Leu Ala Thr Val Leu Met Tyr Val Gln Ser Ala Ala Val Leu
                85                  90                  95

Glu Ile Val His Ala Ala Leu Gly Leu Val Arg Ser Pro Val Phe Val
            100                 105                 110

Thr Thr Met Gln Val Gly Ser Arg Ile Val Ala Leu His Met Leu Ser
        115                 120                 125

Thr Cys Pro Ser Ala Gln Thr Gln Trp Gly Ala Ala Leu Met Ile Phe
    130                 135                 140

Ser Trp Ala Leu Val Glu Val Pro Arg Tyr Leu Phe Tyr Val Ala Ala
145                 150                 155                 160

Ile Val Thr Gly Asp Ala Thr Lys Gly Thr Pro Tyr Pro Leu Phe Trp
                165                 170                 175

Leu Arg Tyr Ser Leu Phe Ala Val Leu Tyr Pro Thr Gly Ile Ser Gly
            180                 185                 190

Glu Leu Ser Val Phe Leu Thr Ser Ala Lys Cys Asp Thr Phe Leu Ser
        195                 200                 205

Thr Leu Gly Glu Ser Asn Lys Ser Ile Met Tyr Trp Tyr Ala Met Ala
    210                 215                 220

Phe Pro Ile Ile Tyr Ala Pro Gly Ala Leu Pro Met Ile Phe Asn Met
225                 230                 235                 240

Val Ala Asn Arg Lys Ser Ala Met Lys Lys Arg Phe Ala Arg Pro Pro
                245                 250                 255

Pro Pro Pro Arg Gly Leu Val Trp Pro Val Thr Glu Thr Lys Ala Asn
            260                 265                 270

Gly Glu Glu Val Arg Ser Ser Thr Pro Val Ala Lys Glu Ile Leu Ala
        275                 280                 285

Ala Ala Ile Gly Ala Val Asn Pro Glu Leu Ala Glu Lys Val Arg Asn
    290                 295                 300

Glu Lys Lys Trp Arg Phe Gly Tyr Gln Lys His Leu Val Asn Met Val
305                 310                 315                 320

Glu Ala Gln Cys Lys Ser Pro Glu Asp Ala Leu Lys Ile Ala Asn Ala
                325                 330                 335

Gly Leu Asn Lys Ala Tyr Met Thr Phe Gln Phe Val Ser Ser Asp Gly
            340                 345                 350

Ser Lys Thr Thr Thr Phe Ala Glu Ala Met Ser Ser Lys Ser Ser Asp
        355                 360                 365
```

-continued

```
Lys Phe His Thr Gly Phe Ile Lys Gly Glu Leu Ala Pro Gln Lys Glu
    370                 375                 380

Lys Lys Leu Glu Val Gly Tyr Lys Gly Lys Gln Ile Ser Gly Asp Glu
385                 390                 395                 400

Leu Lys Ala Gln Val Lys Glu Trp Val Asp Tyr Gly Thr Ile Glu Pro
                405                 410                 415

Ser Ala Gly Glu Ala Ile Cys Ser Cys Val Asp Asn Pro Gly Trp Ile
            420                 425                 430

Asp Leu Ser Asp Arg Tyr Phe Val Leu Leu Gly Ala Gly Ser Ala Met
        435                 440                 445

Gly Pro Phe Glu Val Leu Met Gln Leu Gly Ala Asn Val Ile Gly Ile
    450                 455                 460

Asp Leu Asp Arg Pro Phe Ile Trp Gln Arg Leu Ile Asn Arg Val Met
465                 470                 475                 480

Asn Ser Ser Gly Ser Ile Thr Phe Pro Met Ser Lys Glu Gln Ser Lys
                485                 490                 495

Cys Ala Asp Glu Lys Glu Leu Phe Ala Ala Ser Gly Cys Asn Leu Phe
            500                 505                 510

Thr Gln Ala Pro Met Ile Arg Asp Trp Leu Val Asp Leu Tyr Pro Gly
        515                 520                 525

Lys Ser Phe Thr Val Gly Ser Tyr Ala Tyr Leu Asn Gly Ala Leu His
    530                 535                 540

Val Gln Val Ser Leu Ala Met Asp Ala Ile Cys Arg Asp Leu Cys Asp
545                 550                 555                 560

Lys Arg Lys Asn Thr Ser Leu Ala Tyr Leu Cys Thr Pro Thr Asp Leu
                565                 570                 575

His Leu Ile Pro Lys Glu Ala His Asp Ala Ala Glu Ala Asn Tyr Lys
            580                 585                 590

Glu Phe Ser Lys Lys Pro Phe Cys Met Phe Met Lys Leu Phe Phe Gly
        595                 600                 605

Lys Lys Thr Leu Arg Lys Asn Val Lys Lys Pro Val Ser Gly Val Gly
    610                 615                 620

Gly Asp Phe Tyr Tyr Val Asn Gly Ile Ser Val Ala Gln Gly Pro Asn
625                 630                 635                 640

Tyr Ala Leu Ala Lys Arg Met Gln His Trp Arg Ala Val Ile Ala Arg
                645                 650                 655

Ser Lys Gly Cys Ile Val Ser Ser Asn Ile Ala Pro Ser Thr Ser Thr
            660                 665                 670

Val Ser Val Thr Gln Asn Arg Thr Phe Ala Trp Ala Tyr Glu Gly Met
        675                 680                 685

Pro Tyr Phe Lys Pro Tyr Glu Ile Phe Ala Pro Glu Thr Ser Asn Ser
    690                 695                 700

Val Met Ser Ala Ile Leu Phe Asn Asp Leu Asn Asn His Lys Ser Ile
705                 710                 715                 720

Ala Asn Pro Asp Val Gly Ile Ala Asn Pro Asn Gln Leu Phe Ser Phe
                725                 730                 735

Gly Ala Phe His Gly Gly Thr Trp Arg Cys Ala Tyr Glu Ile Asp Ser
            740                 745                 750

Ile Gly Glu Ala Ser Val Leu Leu Tyr Phe Ser Arg Val Ala Lys Pro
        755                 760                 765

Tyr Ala Ile Ala Phe Gly Gly Leu Gly Leu Ala Ala Gly Ala Lys Trp
    770                 775                 780
```

```
Phe Gly Ile Val
785


<210> SEQ ID NO 3
<211> LENGTH: 2244
<212> TYPE: DNA
<213> ORGANISM: Phaeodactylum tricornutum

<400> SEQUENCE: 3

atgggactta aggacgctta cctcgtgctt tacaactctg cttgttgtgc tggctgggct      60

tatgtttggt acgctgcttg tactactatc ctcgataagg ttgcaaacca gtcacctttc     120

ggtgatgctt ctgctcaagt ttacgctcac gatgatactg ctactatgct tacctacgct     180

caatctgctg ctctccttga gatccttcac gctgctcttg gacttgttag atctcctgtt     240

atggtgaccg ctatgcaagt tatgtctagg atcgttgctc ttgttgctct cgtgttctct     300

tcacaagctc aaactcaatg gggagctgga cttatgatta tctcttgggc ttcagttgaa     360

gttcctcgtt acgctttcta cgttactgct ctccttactg gtgatgctac taagaaaacc     420

cctttccctc ttttctggct tcgttactct cttttcgcta tcctttaccc tactggaatc     480

tgtggagagc ttactgtttt cctcgctgct tctaaggatc aagctttcgt ggataagttc     540

ggacctcttt ctgttactct ctactctatc gttctcccta tcgtgtactt cttcggatct     600

ccttttatga ttatgaatat ggtggctaac agaaagtctg ctttcaagaa gagattcgca     660

aagcctccac ctcctgctag aggactttgt tggcctgttg atgctaaggg acagagatct     720

tctaccaacg tgaacaagac gattattgct gctgctgttg gagctgttaa cgagcaaaag     780

gctgaggcta tcagatcttg taaggcttgg agattccagt acgttaagca ccttagagct     840

atggttgagg aacaatgtca aactcctgag tctgctctta agatcgctca agctggactt     900

gattctgctt acgatatctt cgagttcgtt gctcctgatg gatctgctac tactttcagg     960

gaagctatgg ctgctaagaa cactgagcag ttcttcactc acgttatcaa gggagaggga    1020

aacaagctta ccaaagagct tgagatccct tacaagggtg gaatccttaa gggtgatgct    1080

cttaagaagc aggttcagtc ttgggctgat tacggaacta tcgagccttc tgctggtgct    1140

gctatcgtta agtgtatcga gcaccctgag tggcttgata tcagcaacag atacttcgtt    1200

cttcttggag ctggatctgc tatgggacct cttcttgttc ttatggctct cggagctaac    1260

gttatcgctg tggatcttga tagacctaat atctggaagc gtcttatcga tatcgctaga    1320

caatcttctg gaacgatcac cttccctatg aagatggacc ctagcaagtg taagaacgac    1380

gaggaaatgt tcgctcaggc tggatgtaac cttttcaccg acacccctat gatcagagat    1440

tggttgatga acgtttaccc tggaaagtct cttactgttg gatgctacgc ttaccttgat    1500

ggtgctctcc acgttcaagt ttctcttgct atggatgcta tctgccgtga tctttctgag    1560

aagaggaaga acacttctct tgcttacctc tgcactccta ctgatcttca cttgatccct    1620

aaagaggctc acgatgctat gaaggctaac tacaagtctt actccggaaa gctttactgt    1680

atgatgatga accttctcag cggaggaaag ttccttagac agaactctaa gaagcctgtt    1740

tctggaaagg gtggagagta ctaccttgtg aacggaatct ctgttgctca aggacctaac    1800

tacgctcttg ctaagagaat gcaacactgg cgtgctatca ctgctagaaa caagggatgt    1860

atcgtgtcta gcaatattgc tccttctacc tctaccgttt ctgttgttca caacagaact    1920

ttcgcttggg cttacgaggg aatgccttac ttcgagcctt tcgagatctt cgctcctgag    1980

acttctaacg ctgttatgtc tgctctcctc ttctacgatc tcaacgattc tggatcttgg    2040
```

-continued

```
gctactccta acacttctct cggaaaccct aaccagcttt tctctcacgg atctttccac   2100

ggtggagttt ggagatgtgc ttacgaggtt gactctatcg gagaatcttc tgtgcttctc   2160

tacttcggaa gagtggctaa accttatatg gttgctgctg gtgccgtggc cgcagctggt   2220

gcagcctacg tttacgctgt gtga                                          2244


<210> SEQ ID NO 4
<211> LENGTH: 747
<212> TYPE: PRT
<213> ORGANISM: Phaeodactylum tricornutum

<400> SEQUENCE: 4

Met Gly Leu Lys Asp Ala Tyr Leu Val Leu Tyr Asn Ser Ala Cys Cys
1               5                   10                  15

Ala Gly Trp Ala Tyr Val Trp Tyr Ala Ala Cys Thr Thr Ile Leu Asp
            20                  25                  30

Lys Val Ala Asn Gln Ser Pro Phe Gly Asp Ala Ser Ala Gln Val Tyr
        35                  40                  45

Ala His Asp Asp Thr Ala Thr Met Leu Thr Tyr Ala Gln Ser Ala Ala
    50                  55                  60

Leu Leu Glu Ile Leu His Ala Ala Leu Gly Leu Val Arg Ser Pro Val
65                  70                  75                  80

Met Val Thr Ala Met Gln Val Met Ser Arg Ile Val Ala Leu Val Ala
                85                  90                  95

Leu Val Phe Ser Ser Gln Ala Gln Thr Gln Trp Gly Ala Gly Leu Met
            100                 105                 110

Ile Ile Ser Trp Ala Ser Val Glu Val Pro Arg Tyr Ala Phe Tyr Val
        115                 120                 125

Thr Ala Leu Leu Thr Gly Asp Ala Thr Lys Lys Thr Pro Phe Pro Leu
    130                 135                 140

Phe Trp Leu Arg Tyr Ser Leu Phe Ala Ile Leu Tyr Pro Thr Gly Ile
145                 150                 155                 160

Cys Gly Glu Leu Thr Val Phe Leu Ala Ala Ser Lys Asp Gln Ala Phe
                165                 170                 175

Val Asp Lys Phe Gly Pro Leu Ser Val Thr Leu Tyr Ser Ile Val Leu
            180                 185                 190

Pro Ile Val Tyr Phe Phe Gly Ser Pro Phe Met Ile Met Asn Met Val
        195                 200                 205

Ala Asn Arg Lys Ser Ala Phe Lys Lys Arg Phe Ala Lys Pro Pro Pro
    210                 215                 220

Pro Ala Arg Gly Leu Cys Trp Pro Val Asp Ala Lys Gly Gln Arg Ser
225                 230                 235                 240

Ser Thr Asn Val Asn Lys Thr Ile Ile Ala Ala Ala Val Gly Ala Val
                245                 250                 255

Asn Glu Gln Lys Ala Glu Ala Ile Arg Ser Cys Lys Ala Trp Arg Phe
            260                 265                 270

Gln Tyr Val Lys His Leu Arg Ala Met Val Glu Glu Gln Cys Gln Thr
        275                 280                 285

Pro Glu Ser Ala Leu Lys Ile Ala Gln Ala Gly Leu Asp Ser Ala Tyr
    290                 295                 300

Asp Ile Phe Glu Phe Val Ala Pro Asp Gly Ser Ala Thr Thr Phe Arg
305                 310                 315                 320

Glu Ala Met Ala Ala Lys Asn Thr Glu Gln Phe Phe Thr His Val Ile
                325                 330                 335
```

```
Lys Gly Glu Gly Asn Lys Leu Thr Lys Glu Leu Glu Ile Pro Tyr Lys
            340                 345                 350

Gly Gly Ile Leu Lys Gly Asp Ala Leu Lys Lys Gln Val Gln Ser Trp
        355                 360                 365

Ala Asp Tyr Gly Thr Ile Glu Pro Ser Ala Gly Ala Ala Ile Val Lys
    370                 375                 380

Cys Ile Glu His Pro Glu Trp Leu Asp Ile Ser Asn Arg Tyr Phe Val
385                 390                 395                 400

Leu Leu Gly Ala Gly Ser Ala Met Gly Pro Leu Leu Val Leu Met Ala
                405                 410                 415

Leu Gly Ala Asn Val Ile Ala Val Asp Leu Asp Arg Pro Asn Ile Trp
            420                 425                 430

Lys Arg Leu Ile Asp Ile Ala Arg Gln Ser Ser Gly Thr Ile Thr Phe
        435                 440                 445

Pro Met Lys Met Asp Pro Ser Lys Cys Lys Asn Asp Glu Glu Met Phe
    450                 455                 460

Ala Gln Ala Gly Cys Asn Leu Phe Thr Asp Thr Pro Met Ile Arg Asp
465                 470                 475                 480

Trp Leu Met Asn Val Tyr Pro Gly Lys Ser Leu Thr Val Gly Cys Tyr
                485                 490                 495

Ala Tyr Leu Asp Gly Ala Leu His Val Gln Val Ser Leu Ala Met Asp
            500                 505                 510

Ala Ile Cys Arg Asp Leu Ser Glu Lys Arg Lys Asn Thr Ser Leu Ala
        515                 520                 525

Tyr Leu Cys Thr Pro Thr Asp Leu His Leu Ile Pro Lys Glu Ala His
    530                 535                 540

Asp Ala Met Lys Ala Asn Tyr Lys Ser Tyr Ser Gly Lys Leu Tyr Cys
545                 550                 555                 560

Met Met Met Asn Leu Leu Ser Gly Gly Lys Phe Leu Arg Gln Asn Ser
                565                 570                 575

Lys Lys Pro Val Ser Gly Lys Gly Gly Glu Tyr Tyr Leu Val Asn Gly
            580                 585                 590

Ile Ser Val Ala Gln Gly Pro Asn Tyr Ala Leu Ala Lys Arg Met Gln
        595                 600                 605

His Trp Arg Ala Ile Thr Ala Arg Asn Lys Gly Cys Ile Val Ser Ser
    610                 615                 620

Asn Ile Ala Pro Ser Thr Ser Thr Val Ser Val Val His Asn Arg Thr
625                 630                 635                 640

Phe Ala Trp Ala Tyr Glu Gly Met Pro Tyr Phe Glu Pro Phe Glu Ile
                645                 650                 655

Phe Ala Pro Glu Thr Ser Asn Ala Val Met Ser Ala Leu Leu Phe Tyr
            660                 665                 670

Asp Leu Asn Asp Ser Gly Ser Trp Ala Thr Pro Asn Thr Ser Leu Gly
        675                 680                 685

Asn Pro Asn Gln Leu Phe Ser His Gly Ser Phe His Gly Gly Val Trp
    690                 695                 700

Arg Cys Ala Tyr Glu Val Asp Ser Ile Gly Glu Ser Ser Val Leu Leu
705                 710                 715                 720

Tyr Phe Gly Arg Val Ala Lys Pro Tyr Met Val Ala Ala Gly Ala Val
                725                 730                 735

Ala Ala Ala Gly Ala Ala Tyr Val Tyr Ala Val
            740                 745
```

<210> SEQ ID NO 5
<211> LENGTH: 1371
<212> TYPE: DNA
<213> ORGANISM: Ostreococcus tauri

<400> SEQUENCE: 5

```
atgtgtgttg agaccgagaa caacgatgga atccctactg tggagatcgc tttcgatgga     60

gagagagaaa gagctgaggc taacgtgaag ttgtctgctg agaagatgga acctgctgct    120

ttggctaaga ccttcgctag aagatacgtg gttatcgagg gagttgagta cgatgtgacc    180

gatttcaaac atcctggagg aaccgtgatt ttctacgctc tctctaacac tggagctgat    240

gctactgagg ctttcaagga gttccaccac agatctagaa aggctaggaa ggctttggct    300

gctttgcctt ctagacctgc taagaccgct aaagtggatg atgctgagat gctccaggat    360

ttcgctaagt ggagaaagga gttggagagg gacggattct tcaagccttc tcctgctcat    420

gttgcttaca gattcgctga gttggctgct atgtacgctt tgggaaccta cttgatgtac    480

gctagatacg ttgtgtcctc tgtgttggtt tacgcttgct tcttcggagc tagatgtgga    540

tgggttcaac atgagggagg acattcttct ttgaccggaa acatctggtg ggataagaga    600

atccaagctt tcactgctgg attcggattg gctggatctg gagatatgtg gaactccatg    660

cacaacaagc accatgctac tcctcaaaaa gtgaggcacg atatggattt ggataccact    720

cctgctgttg ctttcttcaa caccgctgtg gaggataata gacctagggg attctctaag    780

tactggctca gattgcaagc ttggaccttc attcctgtga cttctggatt ggtgttgctc    840

ttctggatgt tcttcctcca tccttctaag gctttgaagg gaggaaagta cgaggagctt    900

gtgtggatgt tggctgctca tgtgattaga acctggacca ttaaggctgt tactggattc    960

accgctatgc aatcctacgg actcttcttg gctacttctt gggtttccgg atgctacttg   1020

ttcgctcact tctctacttc tcacacccat ttggatgttg ttcctgctga tgagcatttg   1080

tcttgggtta ggtacgctgt ggatcacacc attgatatcg atccttctca gggatgggtt   1140

aactggttga tgggatactt gaactgccaa gtgattcatc acctcttccc ttctatgcct   1200

caattcagac aacctgaggt gtccagaaga ttcgttgctt tcgctaagaa gtggaacctc   1260

aactacaagg tgatgactta tgctggagct tggaaggcta ctttgggaaa cctcgataat   1320

gtgggaaagc actactacgt gcacggacaa cattctggaa agaccgcttg a            1371
```

<210> SEQ ID NO 6
<211> LENGTH: 456
<212> TYPE: PRT
<213> ORGANISM: Ostreococcus tauri

<400> SEQUENCE: 6

```
Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95
```

```
Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
        435                 440                 445

Gly Gln His Ser Gly Lys Thr Ala
    450                 455


<210> SEQ ID NO 7
<211> LENGTH: 873
<212> TYPE: DNA
<213> ORGANISM: Physcomitrella patens

<400> SEQUENCE: 7

atggaagttg ttgagaggtt ctacggagag ttggatggaa aggtttccca aggagtgaac      60
```

```
gctttgttgg gatctttcgg agttgagttg actgataccc caactactaa gggattgcca    120

ctcgttgatt ctccaactcc aattgtgttg ggagtgtctg tttacttgac catcgtgatc    180

ggaggattgc tttggatcaa ggctagagat ctcaagccaa gagcttctga gccattcttg    240

ttgcaagctt tggtgttggt gcacaacttg ttctgcttcg ctttgtctct ttacatgtgc    300

gtgggtatcg cttaccaagc tatcacctgg agatattcct tgtggggaaa cgcttataac    360

ccaaagcaca aggagatggc tatcctcgtt tacctcttct acatgtccaa gtacgtggag    420

ttcatggata ccgtgatcat gatcctcaag agatccacca gacagatttc tttcctccac    480

gtgtaccacc attcttctat ctcccttatc tggtgggcta ttgctcatca tgctccagga    540

ggagaggctt attggagtgc tgctctcaac tctggagtgc atgtgttgat gtacgcttac    600

tacttcttgg ctgcttgctt gagatcttcc ccaaagctca agaacaagta cctcttctgg    660

ggaagatacc tcacccaatt ccagatgttc cagttcatgc tcaacttggt gcaagcttac    720

tacgatatga aaccaacgct ccatatccaa caatggctca tcaagatcct cttctactac    780

atgatctccc tcttgttcct cttcggaaac ttctacgtgc aaaagtacat caagccatcc    840

gatggaaagc aaaagggagc taagaccgag tga                                  873
```

<210> SEQ ID NO 8
<211> LENGTH: 290
<212> TYPE: PRT
<213> ORGANISM: Physcomitrella patens

<400> SEQUENCE: 8

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
```

```
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290


<210> SEQ ID NO 9
<211> LENGTH: 1320
<212> TYPE: DNA
<213> ORGANISM: Thraustochytrium ssp

<400> SEQUENCE: 9

atgggaaaag gatctgaggg aagatctgct gctagagaga tgactgctga ggctaacgga      60

gataagagaa agaccatcct cattgaggga gtgttgtacg atgctaccaa cttcaaacac     120

ccaggaggtt ccattattaa cttcctcacc gagggagaag ctggagttga tgctacccaa     180

gcttacagag agttccatca gagatccgga aaggctgata agtacctcaa gtccctccca     240

aagttggatg cttctaaggt ggagtctagg ttctctgcta aggagcaggc tagaagggac     300

gctatgacca gggattacgc tgctttcaga gaggagttgg ttgctgaggg atacttcgat     360

ccatctatcc cacacatgat ctacagagtg gtggagattg tggctttgtt cgctttgtct     420

ttctggttga tgtctaaggc ttctccaacc tctttggttt tgggagtggt gatgaacgga     480

atcgctcaag gaagatgcgg atgggttatg catgagatgg gacacggatc tttcactgga     540

gttatctggc tcgatgatag gatgtgcgag ttcttctacg gagttggatg tggaatgtct     600

ggacactact ggaagaacca gcattctaag caccatgctg ctccaaacag attggagcac     660

gatgtggatt tgaacacctt gccactcgtt gctttcaacg agagagttgt gaggaaggtt     720

aagccaggat ctttgttggc tttgtggctc agagttcagg cttatttgtt cgctccagtg     780

tcttgcttgt tgatcggatt gggatggacc ttgtacttgc acccaagata tatgctcagg     840

accaagagac atatggagtt tgtgtggatc ttcgctagat atatcggatg gttctccttg     900

atgggagctt tgggatattc tcctggaact tctgtgggaa tgtacctctg ctctttcgga     960

cttggatgca tctacatctt cctccaattc gctgtgtctc atacccattt gccagttacc    1020

aacccagagg atcaattgca ttggcttgag tacgctgctg atcataccgt gaacatctct    1080

accaagtctt ggttggttac ctggtggatg tctaacctca acttccaaat cgagcatcat    1140

ttgttcccaa ccgctccaca attcaggttc aaggagatct ctccaagagt tgaggctctc    1200

ttcaagagac ataacctccc ttactacgat ttgccataca cctctgctgt ttctactacc    1260

ttcgctaacc tctactctgt tggacattct gttggagctg ataccaagaa gcaggattga    1320


<210> SEQ ID NO 10
<211> LENGTH: 439
<212> TYPE: PRT
<213> ORGANISM: Thraustochytrium ssp

<400> SEQUENCE: 10

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30
```

```
Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435
```

```
<210> SEQ ID NO 11
<211> LENGTH: 1197
<212> TYPE: DNA
<213> ORGANISM: Phytophtora sojae

<400> SEQUENCE: 11

atggctattt tgaaccctga ggctgattct gctgctaacc tcgctactga ttctgaggct      60

aagcaaagac aattggctga ggctggatac actcatgttg agggtgctcc tgctcctttg     120

cctttggagt tgcctcattt ctctctcaga gatctcagag ctgctattcc taagcactgc     180

ttcgagagat ctttcgtgac ctccacctac tacatgatca agaacgtgtt gacttgcgct     240

gctttgttct acgctgctac cttcattgat agagctggag ctgctgctta tgttttgtgg     300

cctgtgtact ggttcttcca gggatcttac ttgactggag tgtgggttat cgctcatgag     360

tgtggacatc aggcttattg ctcttctgag gtggtgaaca acttgattgg actcgtgttg     420

cattctgctt tgttggtgcc ttaccactct tggagaatct ctcacagaaa gcaccattcc     480

aacactggat cttgcgagaa cgatgaggtt ttcgttcctg tgaccagatc tgtgttggct     540

tcttcttgga acgagacctt ggaggattct cctctctacc aactctaccg tatcgtgtac     600

atgttggttg ttggatggat gcctggatac ctcttcttca acgctactgg acctactaag     660

tactggggaa agtctaggtc tcacttcaac ccttactccg ctatctatgc tgatagggag     720

agatggatga tcgtgctctc cgatattttc ttggtggcta tgttggctgt tttggctgct     780

ttggtgcaca ctttctcctt caacaccatg gtgaagttct acgtggtgcc ttacttcatt     840

gtgaacgctt acttggtgtt gattacctac ctccaacaca ccgataccta catccctcat     900

ttcagagagg gagagtggaa ttggttgaga ggagctttgt gcactgtgga tagatcattt     960

ggtccattcc tcgattctgt ggtgcataga atcgtggata cccatgtttg ccaccacatc    1020

ttctccaaga tgcctttcta tcattgcgag gaggctacca acgctattaa gcctctcctc    1080

ggaaagttct acttgaagga taccactcct gttcctgttg ctctctggag atcttacacc    1140

cattgcaagt tcgttgagga tgatggaaag gtggtgttct acaagaacaa gctctag       1197


<210> SEQ ID NO 12
<211> LENGTH: 398
<212> TYPE: PRT
<213> ORGANISM: Phytophtora sojae

<400> SEQUENCE: 12

Met Ala Ile Leu Asn Pro Glu Ala Asp Ser Ala Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

Tyr Val Leu Trp Pro Val Tyr Trp Phe Phe Gln Gly Ser Tyr Leu Thr
            100                 105                 110

Gly Val Trp Val Ile Ala His Glu Cys Gly His Gln Ala Tyr Cys Ser
        115                 120                 125
```

```
Ser Glu Val Val Asn Asn Leu Ile Gly Leu Val Leu His Ser Ala Leu
    130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
    210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
            260                 265                 270

Phe Tyr Val Val Pro Tyr Phe Ile Val Asn Ala Tyr Leu Val Leu Ile
        275                 280                 285

Thr Tyr Leu Gln His Thr Asp Thr Tyr Ile Pro His Phe Arg Glu Gly
    290                 295                 300

Glu Trp Asn Trp Leu Arg Gly Ala Leu Cys Thr Val Asp Arg Ser Phe
305                 310                 315                 320

Gly Pro Phe Leu Asp Ser Val Val His Arg Ile Val Asp Thr His Val
                325                 330                 335

Cys His His Ile Phe Ser Lys Met Pro Phe Tyr His Cys Glu Glu Ala
            340                 345                 350

Thr Asn Ala Ile Lys Pro Leu Leu Gly Lys Phe Tyr Leu Lys Asp Thr
        355                 360                 365

Thr Pro Val Pro Val Ala Leu Trp Arg Ser Tyr Thr His Cys Lys Phe
    370                 375                 380

Val Glu Asp Asp Gly Lys Val Val Phe Tyr Lys Asn Lys Leu
385                 390                 395
```

```
<210> SEQ ID NO 13
<211> LENGTH: 819
<212> TYPE: DNA
<213> ORGANISM: Thalassiosira pseudonana

<400> SEQUENCE: 13

atggatgctt ataacgctgc tatggataag attggagctg ctatcatcga ttggagtgat      60

ccagatggaa agttcagagc tgatagggag gattggtggt tgtgcgattt cagatccgct     120

atcaccattg ctctcatcta catcgctttc gtgatcttgg gatctgctgt gatgcaatct     180

ctcccagcta tggacccata ccctatcaag ttcctctaca acgtgtctca aatcttcctc     240

tgcgcttaca tgactgttga ggctggattc ctcgcttata ggaacggata caccgttatg     300

ccatgcaacc acttcaacgt gaacgatcca ccagttgcta acttgctctg gctcttctac     360

atctccaaag tgtgggattt ctgggatacc atcttcattg tgctcggaaa gaagtggaga     420

caactctctt tcttgcacgt gtaccatcat accaccatct tcctcttcta ctggttgaac     480

gctaacgtgc tctacgatgg agatatcttc ttgaccatcc tcctcaacgg attcattcac     540

accgtgatgt acacctacta cttcatctgc atgcacacca aggattctaa gaccggaaag     600
```

```
tctttgccaa tctggtggaa gtcatctttg accgctttcc aactcttgca attcaccatc    660

atgatgtccc aagctaccta cttggttttc cacggatgcg ataaggtttc cctcagaatc    720

accatcgtgt acttcgtgta cattctctcc cttttcttcc tcttcgctca gttcttcgtg    780

caatcctaca tggctccaaa gaagaagaag tccgcttga                          819


<210> SEQ ID NO 14
<211> LENGTH: 272
<212> TYPE: PRT
<213> ORGANISM: Thalassiosira pseudonana

<400> SEQUENCE: 14

Met Asp Ala Tyr Asn Ala Ala Met Asp Lys Ile Gly Ala Ala Ile Ile
1               5                   10                  15

Asp Trp Ser Asp Pro Asp Gly Lys Phe Arg Ala Asp Arg Glu Asp Trp
            20                  25                  30

Trp Leu Cys Asp Phe Arg Ser Ala Ile Thr Ile Ala Leu Ile Tyr Ile
        35                  40                  45

Ala Phe Val Ile Leu Gly Ser Ala Val Met Gln Ser Leu Pro Ala Met
    50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Tyr Ile Leu Ser Leu Phe Phe Leu Phe Ala
                245                 250                 255

Gln Phe Phe Val Gln Ser Tyr Met Ala Pro Lys Lys Lys Lys Ser Ala
            260                 265                 270


<210> SEQ ID NO 15
<211> LENGTH: 1086
<212> TYPE: DNA
<213> ORGANISM: Phytophtora infestans

<400> SEQUENCE: 15

atggcgacga aggaggcgta tgtgttcccc actctgacgg agatcaagcg gtcgctacct     60

aaagactgtt tcgaggcttc ggtgcctctg tcgctctact acaccgtgcg ttgtctggtg    120
```

```
atcgcggtgg ctctaacctt cggtctcaac tacgctcgcg ctctgcccga ggtcgagagc    180

ttctgggctc tggacgccgc actctgcacg ggctacatct tgctgcaggg catcgtgttc    240

tggggcttct tcacggtggg ccacgatgcc ggccacggcg ccttctcgcg ctaccacctg    300

cttaacttcg tggtgggcac tttcatgcac tcgctcatcc tcacgccctt cgagtcgtgg    360

aagctcacgc accgtcacca ccacaagaac acgggcaaca ttgaccgtga cgaggtcttc    420

tacccgcaac gcaaggccga cgaccacccg ctgtctcgca acctgattct ggcgctcggg    480

gcagcgtggc tcgcctattt ggtcgagggc ttccctcctc gtaaggtcaa ccacttcaac    540

ccgttcgagc ctctgttcgt gcgtcaggtg tcagctgtgg taatctctct tctcgcccac    600

ttcttcgtgg ccggactctc catctatctg agcctccagc tgggccttaa gacgatggca    660

atctactact atggacctgt ttttgtgttc ggcagcatgc tggtcattac caccttccta    720

caccacaatg atgaggagac cccatggtac gccgactcgg agtggacgta cgtcaagggc    780

aacctctcgt ccgtggaccg atcgtacggc gcgctcattg acaacctgag ccacaacatc    840

ggcacgcacc agatccacca ccttttccct atcattccgc actacaaact caagaaagcc    900

actgcggcct tccaccaggc tttccctgag ctcgtgcgca agagcgacga gccaattatc    960

aaggctttct tccgggttgg acgtctctac gcaaactacg gcgttgtgga ccaggaggcg   1020

aagctcttca cgctaaagga agccaaggcg gcgaccgagg cggcggccaa gaccaagtcc   1080

acgtaa                                                              1086
```

<210> SEQ ID NO 16
<211> LENGTH: 361
<212> TYPE: PRT
<213> ORGANISM: Phytophtora infestans

<400> SEQUENCE: 16

```
Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190
```

```
Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360
```

<210> SEQ ID NO 17
<211> LENGTH: 1434
<212> TYPE: DNA
<213> ORGANISM: Claviceps purpurea

<400> SEQUENCE: 17

```
atggctgcta ctacctctgc tatgagcaag gatgctgttc ttagaagaac tgctgctgct      60

actactgcta tcgatcacga aagctctacc tctgcttctc cagctgattc tcctagactc     120

tctgcttctt ctacctctct ctcttctctc agctctctcg acgctaagga taaggatgat     180

gagtacgctg gacttcttga tacttacgga aacgctttca cccctcctga tttcactatc     240

aaggatatca gagatgctat ccctaagcac tgcttcgagc gttctgctat caagggatac     300

gcttatatcc tcagagatgt ggcttgcctt tctaccactt tctacctctt ccacaacttc     360

gttacccctg agaacgttcc ttacacccct cttagagttt tcctctgggg agtttacact     420

gctcttcagg gacttttcgg aactggactc tggattatcg ctcacgagtg tggacacggt     480

gctttctctc cttctaccct cactaacgat cttactggat gggttctcca ctctgctctt     540

ctcgtgcctt acttctcttg gaagttctct cactctgctc accacaaggg aaccggaaat     600

atggaaaggg atatggcttt cctccctaga actagggctc aatacgctac cagattcgga     660

agagctatgg atcagcttgg agatctttgc gaggaaaccc ctatctacac tgctggattc     720

cttgttttcc agcagcttct tggatggcct tcttacttga tcgctaacgt tactggacac     780

gatcttcacg agagacagag agagggaaga ggaaagggaa agaagaacgg attcggagga     840

actgttaacc acttcgaccc tcgttctcct atcttcgatg acaagcacgc taagtttatc     900

gttctcagcg atatcggact tggacttgct atcgctgctc ttgtttacct cggaaacaga     960

ttcggatggg ctaacgttgc tgtttggtac ttcgttcctt acctctgggt taaccactgg    1020

atcgttgcta tcactttcct tcagcacact gatcctactc ttcctcacta cactgctgag    1080

gaatggaact tcgttcgtgg agctgctgct acaatcgata gagagatggg atttatcggt    1140
```

-continued

```
agacacctct tccacggaat cgttgagact cacgtgcttc accactacgt ttcttcaatc   1200

cctttctaca acgctgatga ggcttctgag gctatcaagc ctgttatggg aaagcactac   1260

cgttctgaga ctaaggatgg acctatgggt tttatcaggg ctttgtggaa aactgctaga   1320

tggtgtcaat gggttgagcc ttctgctgat gctcaaggtg ctggtgaagg tgttctcttc   1380

ttcaggaaca gaaacggact tggaactaag cctatctcta tgaggaccca gtga         1434
```

<210> SEQ ID NO 18
<211> LENGTH: 477
<212> TYPE: PRT
<213> ORGANISM: Claviceps purpurea

<400> SEQUENCE: 18

```
Met Ala Ala Thr Thr Ser Ala Met Ser Lys Asp Ala Val Leu Arg Arg
1               5                   10                  15

Thr Ala Ala Ala Thr Thr Ala Ile Asp His Glu Ser Ser Thr Ser Ala
            20                  25                  30

Ser Pro Ala Asp Ser Pro Arg Leu Ser Ala Ser Ser Thr Ser Leu Ser
        35                  40                  45

Ser Leu Ser Ser Leu Asp Ala Lys Asp Lys Asp Asp Glu Tyr Ala Gly
    50                  55                  60

Leu Leu Asp Thr Tyr Gly Asn Ala Phe Thr Pro Pro Asp Phe Thr Ile
65                  70                  75                  80

Lys Asp Ile Arg Asp Ala Ile Pro Lys His Cys Phe Glu Arg Ser Ala
                85                  90                  95

Ile Lys Gly Tyr Ala Tyr Ile Leu Arg Asp Val Ala Cys Leu Ser Thr
            100                 105                 110

Thr Phe Tyr Leu Phe His Asn Phe Val Thr Pro Glu Asn Val Pro Tyr
        115                 120                 125

Thr Pro Leu Arg Val Phe Leu Trp Gly Val Tyr Thr Ala Leu Gln Gly
    130                 135                 140

Leu Phe Gly Thr Gly Leu Trp Ile Ile Ala His Glu Cys Gly His Gly
145                 150                 155                 160

Ala Phe Ser Pro Ser Thr Leu Thr Asn Asp Leu Thr Gly Trp Val Leu
                165                 170                 175

His Ser Ala Leu Leu Val Pro Tyr Phe Ser Trp Lys Phe Ser His Ser
            180                 185                 190

Ala His His Lys Gly Thr Gly Asn Met Glu Arg Asp Met Ala Phe Leu
        195                 200                 205

Pro Arg Thr Arg Ala Gln Tyr Ala Thr Arg Phe Gly Arg Ala Met Asp
    210                 215                 220

Gln Leu Gly Asp Leu Cys Glu Glu Thr Pro Ile Tyr Thr Ala Gly Phe
225                 230                 235                 240

Leu Val Phe Gln Gln Leu Leu Gly Trp Pro Ser Tyr Leu Ile Ala Asn
                245                 250                 255

Val Thr Gly His Asp Leu His Glu Arg Gln Arg Glu Gly Arg Gly Lys
            260                 265                 270

Gly Lys Lys Asn Gly Phe Gly Gly Thr Val Asn His Phe Asp Pro Arg
        275                 280                 285

Ser Pro Ile Phe Asp Asp Lys His Ala Lys Phe Ile Val Leu Ser Asp
    290                 295                 300

Ile Gly Leu Gly Leu Ala Ile Ala Ala Leu Val Tyr Leu Gly Asn Arg
305                 310                 315                 320

Phe Gly Trp Ala Asn Val Ala Val Trp Tyr Phe Val Pro Tyr Leu Trp
```

```
                325                 330                 335

Val Asn His Trp Ile Val Ala Ile Thr Phe Leu Gln His Thr Asp Pro
            340                 345                 350

Thr Leu Pro His Tyr Thr Ala Glu Glu Trp Asn Phe Val Arg Gly Ala
        355                 360                 365

Ala Ala Thr Ile Asp Arg Glu Met Gly Phe Ile Gly Arg His Leu Phe
    370                 375                 380

His Gly Ile Val Glu Thr His Val Leu His His Tyr Val Ser Ser Ile
385                 390                 395                 400

Pro Phe Tyr Asn Ala Asp Glu Ala Ser Glu Ala Ile Lys Pro Val Met
                405                 410                 415

Gly Lys His Tyr Arg Ser Glu Thr Lys Asp Gly Pro Met Gly Phe Ile
            420                 425                 430

Arg Ala Leu Trp Lys Thr Ala Arg Trp Cys Gln Trp Val Glu Pro Ser
        435                 440                 445

Ala Asp Ala Gln Gly Ala Gly Glu Gly Val Leu Phe Phe Arg Asn Arg
    450                 455                 460

Asn Gly Leu Gly Thr Lys Pro Ile Ser Met Arg Thr Gln
465                 470                 475


<210> SEQ ID NO 19
<211> LENGTH: 903
<212> TYPE: DNA
<213> ORGANISM: Ostreococcus tauri

<400> SEQUENCE: 19

atgtctgctt ctggagcttt gttgcctgct attgctttcg ctgcttacgc ttacgctacc      60

tacgcttatg ctttcgagtg gtctcatgct aacggaatcg ataacgtgga tgctagagag     120

tggattggag ctttgtcttt gagactccct gcaattgcta ccaccatgta cctcttgttc     180

tgccttgtgg gacctagatt gatggctaag agggaggctt ttgatcctaa gggattcatg     240

ctcgcttaca acgcttacca aaccgctttc aacgttgtgg tgctcggaat gttcgctaga     300

gagatctctg gattgggaca acctgtttgg ggatctacta tgccttggag cgataggaag     360

tccttcaaga ttttgttggg agtgtggctc cattacaaca ataagtacct cgagttgttg     420

gatactgtgt tcatggtggc taggaaaaag accaagcagc tctctttctt gcatgtgtac     480

catcatgctt tgttgatttg ggcttggtgg cttgtttgtc atctcatggc taccaacgat     540

tgcatcgatg cttatttcgg agctgcttgc aactctttca tccacatcgt gatgtactcc     600

tactacctca tgtctgcttt gggaattaga tgcccttgga agagatatat cacccaggct     660

cagatgttgc aattcgtgat cgtgttcgct catgctgttt tcgtgctcag acaaaagcac     720

tgccctgtta ctttgccttg ggcacaaatg ttcgtgatga caaatatgtt ggtgctcttc     780

ggaaacttct acctcaaggc ttactctaac aagtctaggg gagatggagc ttcttctgtt     840

aagcctgctg agactactag agcaccttct gtgagaagaa ccaggtccag gaagatcgat     900

tga                                                                   903


<210> SEQ ID NO 20
<211> LENGTH: 300
<212> TYPE: PRT
<213> ORGANISM: Ostreococcus tauri

<400> SEQUENCE: 20

Met Ser Ala Ser Gly Ala Leu Leu Pro Ala Ile Ala Phe Ala Ala Tyr
1               5                   10                  15
```

```
Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Val Leu Gly
                85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300
```

<210> SEQ ID NO 21
<211> LENGTH: 1560
<212> TYPE: DNA
<213> ORGANISM: Thraustochytrium ssp

<400> SEQUENCE: 21

```
atgactgttg gatacgatga ggagatccca ttcgagcaag ttagggctca taacaagcca      60

gatgatgctt ggtgtgctat tcatggacac gtgtacgatg ttaccaagtt cgcttctgtt     120

catccaggag gagatattat cttgctcgct gctggaaagg aagctactgt gctctacgag     180

acctaccatg ttagaggagt gtctgatgct gtgctcagaa agtacagaat cggaaagttg     240

ccagatggac aaggaggagc taacgagaag gagaagagaa ccttgtctgg attgtcctct     300

gcttcttact acacctggaa ctccgatttc tacagagtga tgagggagag agttgtggct     360

agattgaagg agagaggaaa ggctagaaga ggaggatacg agttgtggat caaggctttc     420

ttgctccttg ttggattctg gtcctctctt tactggatgt gcaccctcga tccatctttc     480
```

```
ggagctatct tggctgctat gtctttggga gtgttcgctg cttttgttgg aacctgcatc    540
caacatgatg gaaaccatgg agctttcgct caatctagat gggttaacaa ggtggcagga    600
tggactttgg atatgatcgg agcttctgga atgacttggg agttccaaca tgtgttggga    660
catcacccat acactaactt gatcgaggag gagaacggat tgcaaaaggt gtccggaaag    720
aagatggata ccaagttggc tgatcaagag tctgatccag atgtgttctc cacctaccca    780
atgatgagat tgcatccatg gcatcagaag agatggtatc acaggttcca gcatatctac    840
ggaccattca tcttcggatt catgaccatc aacaaggtgg tgactcaaga tgttggagtg    900
gtgttgagaa agaggctctt ccaaatcgat gctgagtgca gatatgcttc cccaatgtac    960
gttgctaggt tctggatcat gaaggctttg accgtgttgt acatggttgc tctcccatgt   1020
tatatgcaag gaccatggca tggattgaag ctcttcgcta tcgctcattt cacttgcgga   1080
gaggttttgg ctaccatgtt catcgtgaac cacattatcg agggagtgtc ttacgcttct   1140
aaggatgctg ttaagggaac tatggctcca ccaaagacta tgcatggagt gaccccaatg   1200
aacaacacta gaaaggaggt tgaggctgag gcttctaagt ctggagctgt ggttaagtct   1260
gtgccattgg atgattgggc tgctgttcaa tgccaaacct ctgtgaactg gtctgttgga   1320
tcttggttct ggaaccattt ctctggagga ctcaaccatc aaatcgagca tcatctcttc   1380
ccaggattgt ctcacgagac ctactaccac atccaagatg tggttcaatc tacctgtgct   1440
gagtacggag ttccatacca acatgagcca tctttgtgga ctgcttactg gaagatgctc   1500
gaacatttga gacaattggg aaacgaggag actcacgagt cttggcaaag agctgcttga   1560

<210> SEQ ID NO 22
<211> LENGTH: 519
<212> TYPE: PRT
<213> ORGANISM: Thraustochytrium ssp

<400> SEQUENCE: 22

Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
        115                 120                 125

Arg Arg Gly Gly Tyr Glu Leu Trp Ile Lys Ala Phe Leu Leu Leu Val
    130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190
```

```
Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
    210                 215                 220

Thr Asn Leu Ile Glu Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
    290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
        355                 360                 365

Val Asn His Ile Ile Glu Gly Val Ser Tyr Ala Ser Lys Asp Ala Val
    370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ala Ser Lys Ser Gly Ala
                405                 410                 415

Val Val Lys Ser Val Pro Leu Asp Asp Trp Ala Ala Val Gln Cys Gln
            420                 425                 430

Thr Ser Val Asn Trp Ser Val Gly Ser Trp Phe Trp Asn His Phe Ser
        435                 440                 445

Gly Gly Leu Asn His Gln Ile Glu His His Leu Phe Pro Gly Leu Ser
    450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
        515
```

<210> SEQ ID NO 23
<211> LENGTH: 1491
<212> TYPE: DNA
<213> ORGANISM: Saccharomyces cerevisiae

<400> SEQUENCE: 23

```
gcgcttaaga tagtgccaaa taccaaaagg cacaggtgca gacgatactt aaacaatagt     60

gctactacgc cacttcgtga aagctaatat ctctttacct tgcatttggg catgttgcaa    120

acaggaggat caaaatacaa atggaatcaa gaatgctctt ctggtatgat actttttgtt    180

tttcttttga gcccatgcgt acatttgagc tgttgaaaca gtcaaaaata aaacggcaaa    240
```

```
taaattgaac ttgaacacaa aagtaaacca aatccaagac caaacttcaa aagtatagtt    300

gggagcaaca aaaagattga aaataccttg attcaatggg acacggatct tagcgttacc    360

atgcttcttt tgatagtcac cccataggcg caatttaatg tggcaataaa agttccatag    420

ttctgaaagc acgaaaagac caattaatgt actcaagtca tccaatttca aatatgaata    480

gtatttgaat aacttagcat tcccaaaggg gaagccgtag ccaaagtaac cgaatgaaat    540

gagaccgctt agaacccagt aatggaaaca atttttgaac aggttgaaaa ttggcatagt    600

agctaaagag aattggtgaa caaataaggt ttcaaataat ctctttccat aatgtcctaa    660

aattaaaaaa tatgcaaccc tgtttaaaaa tggattatag tcggagctag cactgtgcca    720

tctatcaaca actgtgggaa tggtagatag ataataaaaa agggagtgaa ccaagactgg    780

acccaaatac tcacaaaaga agactaatct ccatgaaatt tggggaccca aatctttgat    840

gaagaattcc attgagtcat cagcctcttc ttgaaaaaac gattctgaaa taaccggaac    900

ttgtttagat tccttttgt aggttaatct tatcctgtac ttgctgatat tgtggttatt     960

agcagagatt tttttcaaaa catcatctaa agtaggcttt ttggataagt caatttcagt   1020

gtcccttaac cctttagagc ggctttttat ggtgataggc attttcaaat taaattcaaa   1080

atatgtatct ctctcaaata gctcaattgg tttctagata gctaaataga atataatctt   1140

actgtcctcc gttctgtaaa attcacgctc ttagtccctt ttcataattc cttaactttt   1200

tgcgtacaaa atgatatgtt tattatattt ttcttttttt tttttcaaat tttttctttt   1260

tcttgaaaaa tttttcaaat tggaaagctc atctctcttg aatgtataat actttcttcc   1320

tctaactttc aaaaagtttt acatagccaa gaagttttcc ttacatcggt atactactgt   1380

tatataagtt attcttcgag aaacaattag atatcattca tcggataaat ctaagttgcc   1440

cattgctttc aataactccg atcaaattaa ctcaaatcaa ctaaaacagt a            1491
```

<210> SEQ ID NO 24
<211> LENGTH: 310
<212> TYPE: PRT
<213> ORGANISM: Saccharomyces cerevisiae

<400> SEQUENCE: 24

```
Met Pro Ile Thr Ile Lys Ser Arg Ser Lys Gly Leu Arg Asp Thr Glu
1               5                   10                  15

Ile Asp Leu Ser Lys Lys Pro Thr Leu Asp Asp Val Leu Lys Lys Ile
            20                  25                  30

Ser Ala Asn Asn His Asn Ile Ser Lys Tyr Arg Ile Arg Leu Thr Tyr
        35                  40                  45

Lys Lys Glu Ser Lys Gln Val Pro Val Ile Ser Glu Ser Phe Phe Gln
    50                  55                  60

Glu Glu Ala Asp Asp Ser Met Glu Phe Phe Ile Lys Asp Leu Gly Pro
65                  70                  75                  80

Gln Ile Ser Trp Arg Leu Val Phe Phe Cys Glu Tyr Leu Gly Pro Val
                85                  90                  95

Leu Val His Ser Leu Phe Tyr Tyr Leu Ser Thr Ile Pro Thr Val Val
            100                 105                 110

Asp Arg Trp His Ser Ala Ser Ser Asp Tyr Asn Pro Phe Leu Asn Arg
        115                 120                 125

Val Ala Tyr Phe Leu Ile Leu Gly His Tyr Gly Lys Arg Leu Phe Glu
    130                 135                 140

Thr Leu Phe Val His Gln Phe Ser Leu Ala Thr Met Pro Ile Phe Asn
145                 150                 155                 160
```

```
Leu Phe Lys Asn Cys Phe His Tyr Trp Val Leu Ser Gly Leu Ile Ser
                165                 170                 175

Phe Gly Tyr Phe Gly Tyr Gly Phe Pro Phe Gly Asn Ala Lys Leu Phe
            180                 185                 190

Lys Tyr Tyr Ser Tyr Leu Lys Leu Asp Asp Leu Ser Thr Leu Ile Gly
        195                 200                 205

Leu Phe Val Leu Ser Glu Leu Trp Asn Phe Tyr Cys His Ile Lys Leu
    210                 215                 220

Arg Leu Trp Gly Asp Tyr Gln Lys Lys His Gly Asn Ala Lys Ile Arg
225                 230                 235                 240

Val Pro Leu Asn Gln Gly Ile Phe Asn Leu Phe Val Ala Pro Asn Tyr
                245                 250                 255

Thr Phe Glu Val Trp Ser Trp Ile Trp Phe Thr Phe Val Phe Lys Phe
            260                 265                 270

Asn Leu Phe Ala Val Leu Phe Leu Thr Val Ser Thr Ala Gln Met Tyr
        275                 280                 285

Ala Trp Ala Gln Lys Lys Asn Lys Lys Tyr His Thr Arg Arg Ala Phe
    290                 295                 300

Leu Ile Pro Phe Val Phe
305                 310
```

<210> SEQ ID NO 25
<211> LENGTH: 1042
<212> TYPE: DNA
<213> ORGANISM: Saccharomyces cerevisiae

<400> SEQUENCE: 25

```
gaaataatac taattaaata attctaataa ttctaatatt aataacaata ataataagaa      60

taataattat acaataacac atgtatttcc taactcacaa tcgtttggac tacatatgct     120

gtctagtgcc ttattgcgac tttgcccgtt tgataactta cttcgattgt ttagtattca     180

aaaaggaaaa aggcgttttc tttttcgtgt acttttttc gaaattctgt tgaatttatt      240

cgaactcaga attggtccat caagagcatc caaaatacaa aataactcat catcacacaa     300

gaagaagcac aactccaagc aatttctaca atatgtcaaa aaaacttgcg tcaccattgt     360

ccttcttacc cctttataat ttgctttctg ctgttggttg gtcttatttg ctttacttgg     420

tcatctcctt gtacccaaaa gttggacagc cagcattctt ctaccaaact aaaaatgtcg     480

ctacccttgt tcaatgtggt gctataatcg agatcataaa ctcattttta ggagttgtac     540

gttccccatt gctgaccact gttgcacaag tgtcttcaag actactagtt gtcctcggca     600

tcttccaatt gttgccaaac acaagtggtg ttcaatcagt tgtttacata tcattattac     660

tggcatggtc tataactgag atcgtcagat acttgtatta tttttcatg ttggtattca      720

agaatggcgc accaaagatc ttaattctat taagatataa tttgttctgg attttgtacc     780

ccactggtgt tgccagcgaa ctacgcatta tttactgtgc tttaaatgca gctgaatctc     840

agtattcttt actttacaaa agaattttaa tagcggccat gctcgcttat atcccaggct     900

tcccaatgct cttcctacac atggtagcac agagaaagaa agtcatgaaa agtttaagat     960

cctctttcgg gaagaaacta atttgaattc tttagataaa ttcttctgta tttttataa     1020

gaatattagc cttcacattg aa                                             1042
```

<210> SEQ ID NO 26
<211> LENGTH: 217
<212> TYPE: PRT
<213> ORGANISM: Saccharomyces cerevisiae -continued

```
<400> SEQUENCE: 26

Met Ser Lys Lys Leu Ala Ser Pro Leu Ser Phe Leu Pro Leu Tyr Asn
1               5                   10                  15

Leu Leu Ser Ala Val Gly Trp Ser Tyr Leu Leu Tyr Leu Val Ile Ser
            20                  25                  30

Leu Tyr Pro Lys Val Gly Gln Pro Ala Phe Phe Tyr Gln Thr Lys Asn
        35                  40                  45

Val Ala Thr Leu Val Gln Cys Gly Ala Ile Ile Glu Ile Ile Asn Ser
    50                  55                  60

Phe Leu Gly Val Val Arg Ser Pro Leu Leu Thr Thr Val Ala Gln Val
65                  70                  75                  80

Ser Ser Arg Leu Leu Val Val Leu Gly Ile Phe Gln Leu Leu Pro Asn
                85                  90                  95

Thr Ser Gly Val Gln Ser Val Val Tyr Ile Ser Leu Leu Leu Ala Trp
            100                 105                 110

Ser Ile Thr Glu Ile Val Arg Tyr Leu Tyr Tyr Phe Phe Met Leu Val
        115                 120                 125

Phe Lys Asn Gly Ala Pro Lys Ile Leu Ile Leu Leu Arg Tyr Asn Leu
    130                 135                 140

Phe Trp Ile Leu Tyr Pro Thr Gly Val Ala Ser Glu Leu Arg Ile Ile
145                 150                 155                 160

Tyr Cys Ala Leu Asn Ala Ala Glu Ser Gln Tyr Ser Leu Leu Tyr Lys
                165                 170                 175

Arg Ile Leu Ile Ala Ala Met Leu Ala Tyr Ile Pro Gly Phe Pro Met
            180                 185                 190

Leu Phe Leu His Met Val Ala Gln Arg Lys Lys Val Met Lys Ser Leu
        195                 200                 205

Arg Ser Ser Phe Gly Lys Lys Leu Ile
    210                 215
```